United States Patent [19]
Gerardy-Schahn et al.

[11] Patent Number: 5,849,904
[45] Date of Patent: Dec. 15, 1998

[54] ISOLATED NUCLEIC ACID MOLECULES WHICH HYBRIDIZE TO POLYSIALYL TRANSFERASES

[75] Inventors: Rita Gerardy-Schahn, Hiddenhausen, Germany; Minoru Fukuda, San Diego, Calif.; Jun Nakayama, Matsumoto, Japan; Matthias Eckhardt, Hanover, Germany

[73] Assignees: Boehringer Mannheim GmbH, Mannheim, Germany; La Jolla Cancer Research Foun., La Jolla, Calif.

[21] Appl. No.: 576,775

[22] Filed: Dec. 21, 1995

Related U.S. Application Data

[63] Continuation-in-part of Ser. No. 503,133, whihc is a continuation-in-part of PCT/EP94/04289 Dec. 22, 1994.

[30] Foreign Application Priority Data

Oct. 18, 1995 [DE] Germany ......................... 95 116 387.2

[51] Int. Cl.$^6$ .............................. C07H 21/04; C12Q 1/68
[52] U.S. Cl. .................. 536/24.31; 536/23.1; 536/24.32; 435/6
[58] Field of Search ................................ 514/44; 436/94; 536/23.1, 24.5, 24.31, 24.32; 435/6

[56] References Cited

U.S. PATENT DOCUMENTS 5,585,479 12/1996 Hoke et al. ............................ 536/24.5

FOREIGN PATENT DOCUMENTS

WO9318157 9/1993 WIPO .

OTHER PUBLICATIONS

Westermann et al., Inhibition of expression of SV–40 virus large T–antigen by antisense oligodeoxyribonucleotides, Biomed. Biochim. Acta, vol. 48(1), pp. 85–93, 1989.

James, Towards gene inhibition therapy: a review of progress and prospects in the field of antiviral antisense nucleic acids and ribozymes, Antiviral Chemistry and Chemotherapy, vol. 2(4), pp. 191–214, 1991.

Uhlmann et al., Antisense oligonucleotides: a new therapeutic principle, Chemical Reviews, vol. 90(4), pp. 543–584, Jun. 1990.

Weiss, Upping the antisense ante, scientist bet on profits from reverse genetics, Science News, vol. 139, pp. 108–109, Feb. 1991.

Tseng et al., Antisense oligonucleotide technology in the development of cancer therapeutics, Cancer Gene Therapy, vol. 1(1), pp. 65–71, Mar. 1994.

Gewirtz et al., Facility oligonucleotide delivery: helping antisense deliver on its promise, Proc. Natl. Acad. Sci., vol. 93, pp. 3161–3163, Apr. 1996.

Cho et al., "Polysialic acid engineering Synthesis of Polysialalylated neoglycosphingo lipids by using the polysiayltransferase from neuroinvasive Escherichia coli K1", Proc. Natl. Acad. Sci. USA 91: 11427–11431 (Nov. 1994).

Edwards et al., "Molecular analysis of the biosynthesis pathway of the α–2,8 polysialyl acid capsule of Neisseria mengitidis serogroup B", Microbiol. 14(1):141–149 (1994).

Luringston et al., "Polymerase Chain Reaction Cloning of A Developmentally Regulated Member of the Sialyltransferase Gene Family", J. Bio. Chem. 268(16): 11504–11507 (1993).

Steenbergen et al., "Functional Analysis of the Sialytransferase Complexes In Escherichia Coli K1 and K92", J. Bacteriol. 174(4):1099–1108 (1992).

Frosch et al., "Evidence For A Common Molecular Origin of the Capsule Gene Loci In Gram Negative Bacteria Expressing Group II Capsular Polysaccharides", Mol. Microbiol. 5(5): 1251–1263 (1991).

Weisberger et al., Complete Nucleotide And Deduced Protein Sequence of CMP–NeuAc: poly α02,8–sialylosyl sialyltransferase of Escherichia coli K1, Glycobiology 1(4):357–365 (1991).

Kitazume et al., "Developmental Expression of Trout Egg Polysialoglycoproteins And The Prerequisite α2,6 and –60 2,8–Polysialyl Transferase Activities Required For Their Synthesis During Oogenesis", J. Biol. Chem. 269(14): 10330–10340 (1994).

Eckhardt et al., "Molecular Characterized of Eukaryotic Polysialyl transferase–1", Nature 373: 715–718 (Feb. 23, 1995).

Yoshida et al., "Molecular Cloning And Characterization of a Third Type of N–Glycan α2,8–Sialyltansferase From Mouse Lung", J. Biochem. 118: 658–664 (1995).

Gerardy–Schahn et al., "Molecular Cloning And Functional Expression of Bacteriophase PK1E–encoded endoneuramindase Endo NE", Mol. Microbiol. 16(3): 441–450 (1995).

Nara et al., "Expression Cloning of a CMP–NeuAc: NeuAc α2–3 Galβ1 4Glcβ1–1'Cerα2,8 sialyltransferase (GD3 Synthease) from human melanoma cells", Proc. Natl. Acad. Sci. USA 91: 7951–7956 (Aug. 1994).

Kitagawa et al., "Differential Expression of Five Sialyltransferase Genes in Human Tissue", J. Biol. Chem. 269 (27): 17872–17878 (1994).

*Primary Examiner*—John L. LeGuyader
*Assistant Examiner*—Andrew Wang
*Attorney, Agent, or Firm*—Felfe & Lynch

[57] ABSTRACT

Isolated nucleic acid molecules encoding polysialyl transferases, and the polysialyl transferases themselves are disclosed. SEQ ID NOS: 1, 2, 7 and 8 present examples of these. The nucleic acid molecules and the proteins can be used diagnostically or therapeutically. Additionally, antisense oligonucleotides and antibodies are described, which can also be used diagnostically or therapeutically.

8 Claims, 7 Drawing Sheets

FIG. 4A
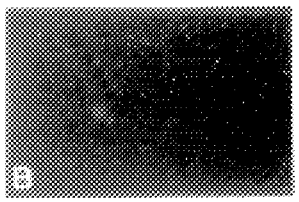
FIG. 4B
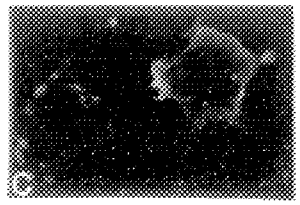
FIG. 4C
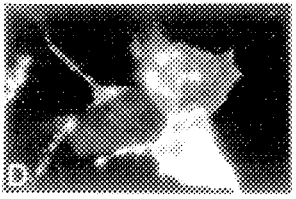
FIG. 4D
FIG. 4E
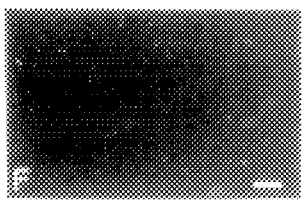
FIG. 4F
FIG. 4G

ISOLATED NUCLEIC ACID MOLECULES WHICH HYBRIDIZE TO POLYSIALYL TRANSFERASES

RELATED APPLICATIONS

This application is a continuation-in-part of U.S. patent application Ser. No. 08/503,133 filed on Jul. 17, 1995, which is a continuation-in-part of PCT Application PCT/EP94/04289 filed on Dec. 22, 1994 designating the United States. Thus, priority is claimed pursuant to 35 U.S.C. §365(a), (b) and (c).

Funds from NIH Grant CA 33895 were used in the development of portions of the invention described herein. Thus the U.S. government may have rights to portions of this invention.

FIELD OF THE INVENTION

This invention relates to the isolation and cloning of nucleic acid molecules which encode polysialyl transferases, cell lines and vectors containing such molecules, and the uses of these. Further the invention relates to the isolated enzyme and its uses. Various diagnostic and therapeutic applications are included as part of the field of the invention, including stimulation of neurite outgrowth by appropriate cells.

BACKGROUND AND PRIOR ART

Polysialic acid (PSA) is added to the neural cell adhesion molecule, NCAM in a dynamically regulated, posttranslational process (S. Hoffman and G. M. Edelman, Proc. Natl. Acad. USA 80: 5762–5766 (1983), U. Rutishauser et al., Science 240: 53–57 (1988)). The glycan structure is unusual in vertebrates and has been shown to be attached to the fifth immunoglobulin domain (K. L. Crossin et al., J. Cell Biol. 99: 1848–1855 (1984)). The presence of the large anionic carbohydrate structure that is PSA modulates NCAM binding properties and, by increasing the intercellular space, also influences interactions between other cell surface molecules (S. Hoffman and G. M. Edelman, supra, U. Rutishauser et al., supra, A. Acheson et al., J. Cell Biol. 114: 143–153 (1991), P. Yang et al., J. Cell. Biol. 116: 1487–1496 (1992), P. Doherty et al., Neuron 5: 209–219 (1990)). In the course of embryogenesis the expression of PSA underlies cell type and developmental-specific alterations (G. M. Edelman, Ann. Rev. Cell Biol. 2: 81–116 (1986)) and correlates with stages of cellular motility (G. M. Edelman, supra (1986)), J. Tang et al., Neuron 8: 1031–1044 (1992), L. Landmesser, J. Neurobiol. 23: 1131–1139 (1992)). In the adult, PSA is restricted to regions of permanent neural plasticity and regenerated neural and muscle tissues (G. M. Edelman. supra), R. Martini and M. Schachner, J. Cell Biol. 106: 1735–1746 (1988), J. K. Daniloff et al. J. Cell Biol. 103: 929–945 (1986)). Recent data implicate PSA in spatial learning and memory (H. Cremer et al., Nature 367: 455–459 (1994), H. Tomasiewicz et al., Neuron 11: 1163–1174 (1993)). Of utmost clinical relevance are the observations that polysialylated NCAM forms represent oncodevelopmental antigens in neuroendocrine and hematolymphoid tumors (C. E. C. K. Moolenaar et al., Canc. Res. 50: 1102–1106 (1990), K. Takamatzu et al., Canc. Res. 54: 2598–2603 (1994), P. Komminoth et al., Ann. J. Patho. 139: 297–304 (1991), W. F. Kern et al., Leukemia & Lymphoma 12: 1–10 (1993)). PSA expression enhances the metastatic potential of these tumors and promotes an abnormal localization of metastases (W. F. Kern et al., supra, E. P. Scheidegger et al., J. Lab. Invest. 70: 45–106 (1994)).

Studies aimed at enlightening the biosynthetic pathway and the regulation of PSA synthesis suggest the concerted activity of several specific enzymes located within the Golgi apparatus (R. D. McCoy et al., J. Biol. Chem. 260: 12659–12699 (1984), S. Kitazume et al., J. Biol. Chem. 269: 10330–10340 (1994)).

In recent years several mammalian sialyltransferases have been cloned (K. Nara et al., Proc. Natl. Acad. Sci. USA 91: 7952–7956 (1994), H. Kitagawa and J. C. Paulson, J. Biol. Chem. 269: 17875–17878 (1994), K. Sasaki et al., J. Biol. Chem. 269: 15950–15956 (1994) and literature cited therein). All enzymes characterized to date are monosialyltransferases which are specific for both the type of glycosidic linkage and the acceptor structure to which the sialic acid is attached. In fact, the synthesis of PSA in rainbow trout eggs has recently been reported to involve the consecutive activity of several specific enzymes (S. Kitazume, supra). Livingston and Paulson, J. Biol. Chem. 268: 11504–11509 (1993) describe a rat sialyl transferase "STX" which shows homology to the hamster polysialyl transferase (PST) described herein, of about 59%. The human STX sequence is shown in the GenBank™ EMBL Data Bank under Accession Number L13445. However, STX does not catalyze any polysialyl reaction.

Three bacterial polysialyl transferases are known (M. Frosch et al., Mol. Microbiol. 5: 1251 (1991); C. Weisgerber et al., Glycobiol. 1: 357 (1991), and S. M. Steenbergen et al., J. Bacteriol. 174: 1099 (1992)). These polysialyl transferases have a substrate and acceptor specificity which is different from the specificity of the enzymes of the invention and do not exhibit any sequence homology with the polysialyl transferases, set forth in the disclosure which follows.

In mammals, particularly humans, PSA is a critical element in the modulation of NCAM binding activities. Thus, there is a need to elucidate, to regulate, and to modulate PSA synthesis, thereby modulating normal and pathological processes which involve, inter alia, NCAM binding.

SUMMARY OF THE INVENTION

The subject matter of the invention is the isolation and molecular cloning of the key enzyme of eukaryotic PSA synthesis, i.e., polysialyl transferase ("PST", hereafter), and the isolation of nucleic acid molecules which encode this enzyme. More specifically, the invention relates to those nucleic acid molecules encoding mammalian PST enzymes, including hamster, human and other species. Especially preferred are nucleic acid molecules which hybridize to SEQ ID NOS: 1 and 7 and portions thereof, especially under stringent conditions, as set forth below.

An additional aspect of the invention is a method of detecting nucleic acid molecules which specifically code for PST proteins. Preferably detected are cDNA and mRNA species. Useful probes are nucleic acid molecules which bind specifically under the conditions of the test method applied, e.g. in situ hybridization, colony hybridization, Northern hybridization, or related techniques.

A further aspect of the invention is an oligonucleotide molecule which is complementary to a nucleic acid molecule encoding mammalian PST. Such oligonucleotide molecules, which are generally from 15 to 50 bases in length, are useful for inhibiting expression of PST, preferably on the DNA or mRNA level. Such oligonucleotide molecules are useful as antisense agents in the therapy of pathological conditions involving a tumor, especially in the treatment and prevention of metastases.

Yet another aspect of the invention involves isolated PST enzymes, such as mammalian PST enzymes, which may be encoded by the isolated nucleic acid molecules of the invention, the production of said enzymes via recombinant methodologies, and the use of the enzymes in promoting neurite growth in nerve cells.

Method: 1×107 cells were harvested, membrane proteins extracted with lysis buffer (20 mM Tris/HCl, pH 8; 1% NP40) and NCAM was immunopurified on a protein A bound anti-NCAM antibody (mab KD11). Samples were separated by 7.5% SDS-PAGE, blotted onto nitrocellulose membranes, and in developed parallel with either biotinylated MAA or anti-NCAM mab KD11. Protein bands were visualized using alkaline phosphatase conjugated streptavidin.

Figure 2:
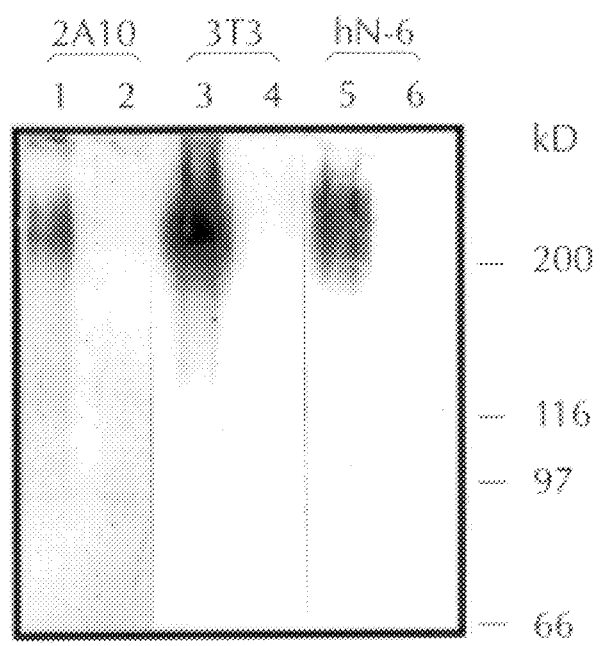

FIG. 2 The PSA found on the surface of pEPST-ME7 transfectants is bound to NCAM. Cells with the phenotype NCAM+/PSA− were transfected with pEPST-ME7 or pCDM8 alone, as described infra, harvested, and solubilized in lysis buffer, NCAM was immunoprecipitated from the lysates using an anti-NCAM serum, and the samples were analyzed by Western blot with mAb 735. Microheterogenous bands became visible in PST transfectants (lane 1: CHO-2A10; lane 3: NIH-3T3; lane 5 COS-hN-6) indicating that NCAM in these cells is polysialylated. In contrast, control transfection with pCDM8 did not result in appearance of mab 735 epitopes (lane 2: CHO-2A10; lane 4: NIH-3T3; lane 6: COS-hN-6).

Figure 3A:
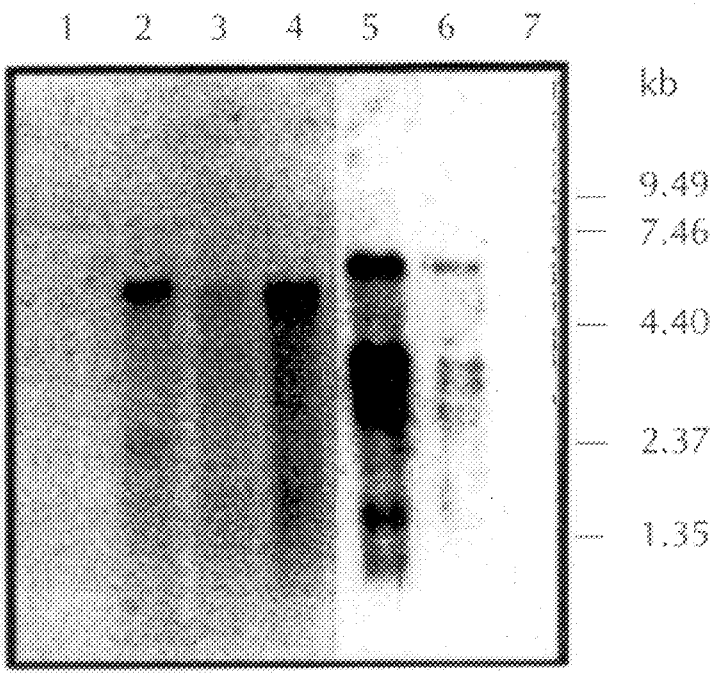

FIG. 3a The Northern blot analysis of pEPST-ME7 transcripts revealed two bands of 5.1 kb and 2.1 kb in the PSA positive CHO-wt cells (lane 2), and in adult (lane 3) and postnatal day 1 mouse brain (lane 4). In accordance with the reduced PSA expression in adult brain, a very faint band was obtained (lane 3). No signal was found with PSA negative NIH-3T3 cells (lane 1). In clonal sublines of the human small cell lung cancer cell line HTB119 a complex pattern with 6 hybridization signals of about 6.1 kb; 3.8 kb; 3.3 kb; 3 kb; 1.7 kb; and 1.3 kb appeared in the highly polysialylated clone HTB119-54.2 (lane 5) and in clone HTB119-38 (lane 6) which expresses low levels of PSA, but was not visible in the PSA-negative subline HTB119-45 (lane 7). The probe used contains the entire coding region of PST.

Figure 3B:
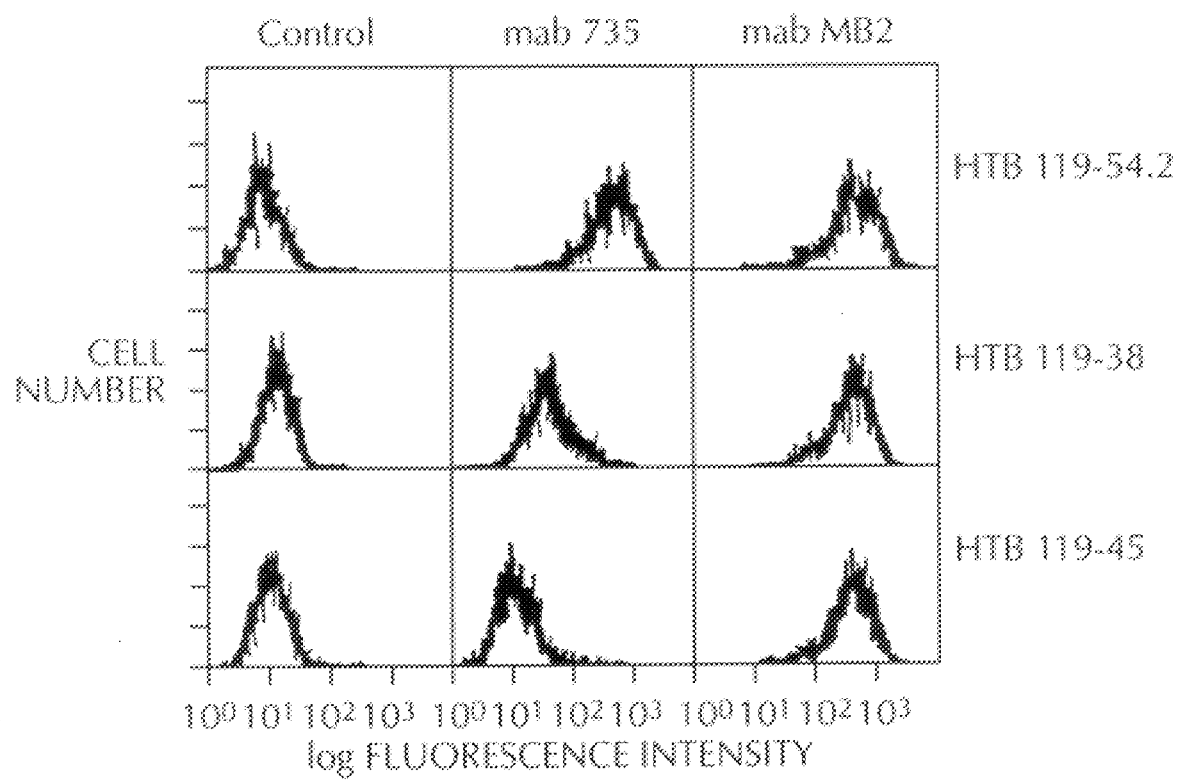

FIG. 3b FACS analysis of sublines isolated by limiting dilution from the small cell lung cancer cell line HTB119. While staining with mab MB2 (specifically directed against human NCAM), indicates that NCAM expression on the 3 sublines is almost identical, the staining with mAb 735 reveals large differences in the amount of detectable PSA. HTB119-54.2 are about 100% PSA positive, in the subline HTB119-38 only 30% of the cells express PSA, and in HTB119-45 the number of PSA expressing cells is reduced to 2%. Immunostaining was performed as described in FIG. 1a.

Method: Poly A+RNA samples (3 ug each lane) were blotted onto nylon membranes and analyzed with a digoxigenin (Boehringer Mannheim) labeled RNA-probe that contained the entire coding region of pEPST-ME7. Final washing conditions were 0.1 x SSC, 0.1% SDS, and 65° C.

FIGS. 4A–4G depict results obtained in various experiments wherein eukaryotic cells were cotransfected with pHβA-NCAM and one of pcDNAI-PST or pcDNAI. (These, and all other acronyms, are elaborated upon in the examples). In FIGS. 4A–F, COS-1 cells were co-transfected with pcDNAI-PST (panels C–F) or pcDNAI (panels A and B) and pHβA-NCAM. Sixty-four hours after transfection, the cells were fixed and examined by incubation with anti-PSA antibody 735 (panels B, D and F) or anti-NCAM antibody (Dako Co. Carpenteria, Calif.) (panels A, C, and E) followed by FITC-conjugated anti-mouse IgG. Samples of COS-1 cells co-transfected with pcDNAI-PST and pHβA-NCAM were also treated with endo-N in the presence of protease inhibitors before applying antibody 735 (panels E and F). Bar=20 $\mu$m. In FIG. 4G, cell lysates from $2.0 \times 10^6$ untransfected HeLa cells (lane 1) or HeLa cells stably co-transfected with pcDNAI-PST and pHβA-NCAM (lanes 2 and 3) were subjected to sodium dodecyl sulfate polyacrylamide (6.5%) gel electrophoresis under reducing conditions, transferred to nitrocellulose and incubated with anti-NCAM antibody (Becton-Dickinson) as described by Fredette et al [(1993). J. Cell Biol. 123: 1867–1888]. The immuno reaction was visualized by ECL Western Blotting analysis system (Amersham, Arlington Heights, Ill.). Lysates of transfected cells were either treated with endo-N prior to electrophoresis (lane 3) or untreated (lane 2).

Figure 5:
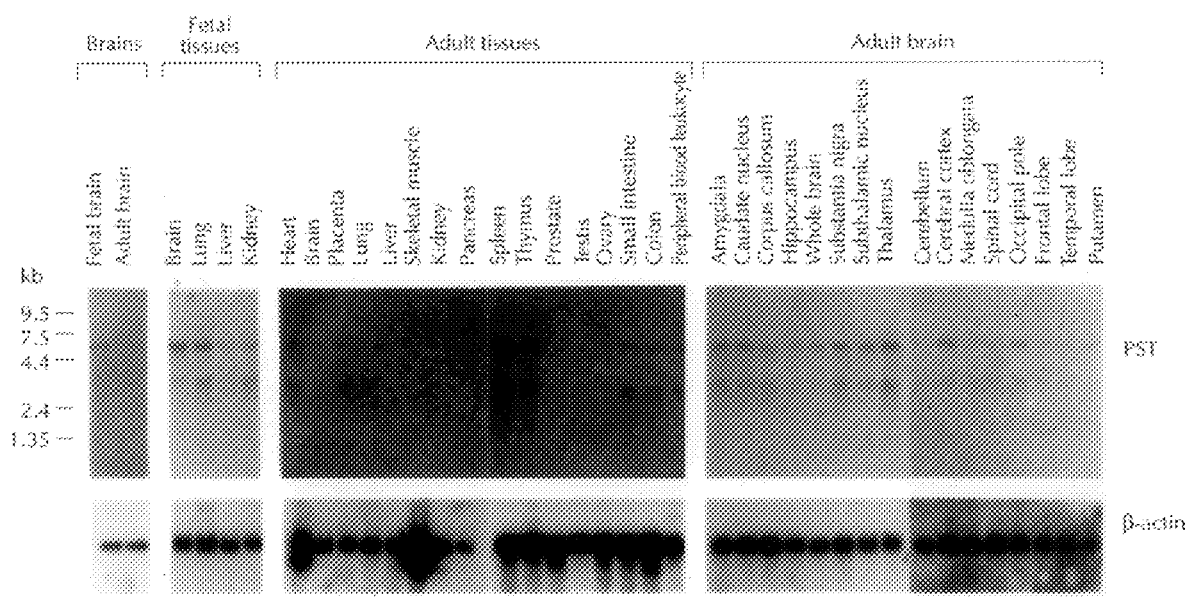

FIG. 5 sets forth results obtained following Northern Blot analysis of various human tissues, to determine expression of PST. Each lane contained 2 ug of poly(A)$^+$ RNA. The blots for the first two lanes at the far left were prepared separately and contained less RNA than the blots of the remaining lanes.

The blots were hybridized with [$^{32}$P]-labeled human PST cDNA, as well as β-actin cDNA as a control.

FIGS. 6A–6D show results obtained from immunohistochemical analysis of various human fetal, newborn, and adult tissues to determine if PSA was expressed therein. Paraffin-embedded sections of tissue were stained with antibody 735 by an avidin-biotin-peroxidase complex method: (A) fetal cerebral cortex, (B) fetal lung, (C) newborn thymus and (D) adult liver.

B=100 µm.

FIGS. 7A–7F set forth the result of experiments designed to determine neurite outgrowth in confluent HeLa cell substrata. Neurons from embryonic day 10 chick dorsal root ganglia (panels A, B C) or embryonic day 6 ventral spinal cord (panes D, E and F) were seeded on HeLa cell substrata and cultured for 15 hours. Neurons shown in panels A and D were grown on untransfected HeLa cells. Neurons shown in panels B and E were grown on HeLa cells stably transfected with N-CAM-encoding DNA only. Neurons shown in panels C and F were grown on HeLa cells cotransfected with DNAs encoding N-CAM and human PST. Neurites were visualized by immunofluorescent neurofilament-staining. Bar=100 µm.

DETAILED DESCRIPTION OF PREFERRED EMBODIMENTS

In reconstitution experiments it has been shown that PST is able to induce PSA synthesis in all NCAM expressing cell lines tested. Furthermore, the soluble, recombinant PST is active in vitro. The data presented herein show that the polycondensation of α-2,8-linked sialic acids in mammals is the result of the activity of a single enzyme. Furthermore, since Northern blot analysis confirmed the close correlation between cell surface expression of PSA and the presence of PST mRNA, this enzyme provides a useful target structure for cancer therapy, as do the nucleic acid molecules, when presented, e.g., as antisense oligonucleotides.

The nucleotide sequences according to the invention encode a protein that functions in the final step of PSA biosynthesis. The close correlation between cell surface expression of PSA and the occurrence of the PST specific mRNA implies that the regulation of PST occurs predominantly on the mRNA level. PST seems to be the primary factor involved in polycondensation of sialic acids during mammalian PSA synthesis and is unique in PSA positive cells. Confirmation for this assumption comes from the fact that expression in the NCAM positive cell lines tested resulted in biosynthesis of PSA. These data together with the observation that PSA surface expression enhances the metastatic potential of neuroendocrine tumors (W. F. Kern et al., supra, E. P. Scheidegger et al., supra) show that PST may be used as a target for tumor therapy and diagnosis. Additional data presented herein suggest the use of PST to stimulate neurite outgrowth on neural cells.

EXAMPLE 1

Figure 1A:
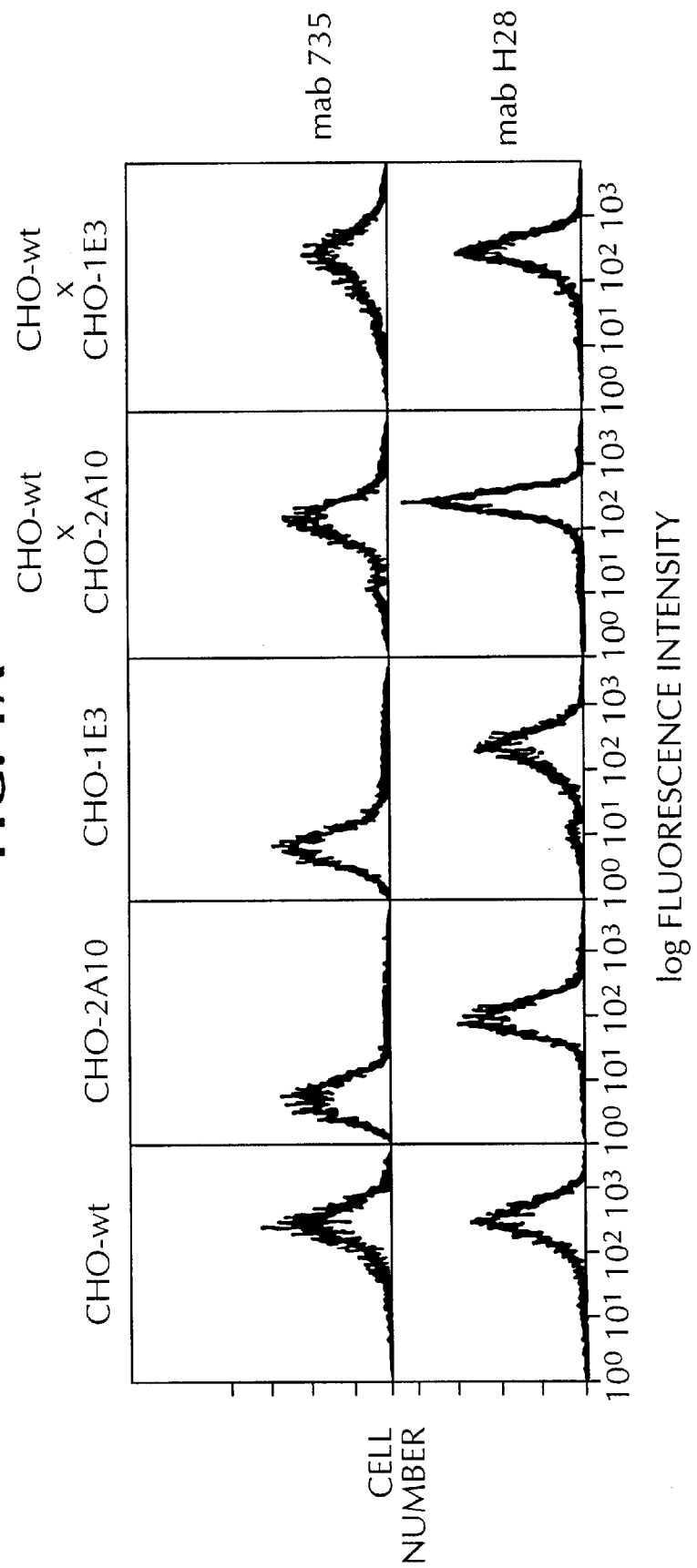
FIG. 1a FACS-analysis of CHO-wt and mutant clones. Staining with the mouse-NCAM specific mAb H28 indicates that NCAM surface expression in the mutant cell lines CHO-2A10 and CHO-1E3 (defective in sialic acid transport) is almost identical to that observed in CHO-wt cells. In contrast, the reactivity with the PSA specific mAb 735 (M. Frosch et al., Proc. Natl. Acad. Sci. USA 82: 1194–1998 (1985)) is restricted to the CHO-wt cells. In order to obtain the hybrid cells CHO-2A10×WT and CHO-2A10×CHO-1E3, a neomycin resistance gene was introduced into clone CHO-2A10 and a hygromycin resistance gene was introduced into CHO-wt and CHO-1E3 cells, respectively. Equal amounts of the two relevant cell types were plated into cell culture dishes and cell fusion was induced by polyethylenglycol (50% PEG 1500 in 50 mM Hepes buffer pH 7.4). Double positive hybrids were selected with G418 and hygromycin. While the NCAM signal in hybrid cells was identical to that observed in parental cells, both fusion products expressed the 735 epitope.
Figure 1B:
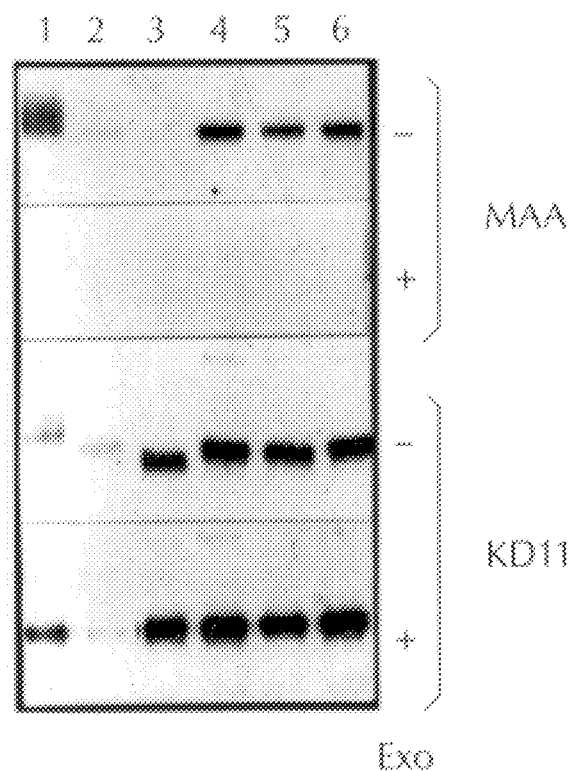
FIG. 1b In order to determine whether a-2,3-sialylation is a prerequisite in PSA biosynthesis, CHO-wt cells and chemically induced mutants were analyzed with Maackia amurensis lectin ("MAA"), which specifically recognizes sialic acid linkage to galactose via an $\alpha$-2, 3 bond. Extracts are shown before (−) and after (+) treatment with exoneuraminidase. Due to polysialylation, both MAA and the anti-NCAM mAb KD11 recognized microheterogenous bands in CHO-wt cells (lanes 1 and 2; wt-cells in two concentrations), while discrete protein bands became visible in PST-C1 mutants (lanes 4–6; 3 individual mutants: 2A10, 1H8, and 3A7). In contrast, mutant CHO-1E3, which is defective in sialic acid transport (lane 3) did not react with MAA and, in accordance with the deficiency of sialylated proteins, the polypeptide band recognized by KD11 in this mutant, showed a significantly reduced Mr. Treatment with exoneuraminidase abolished MAA reactivity completely and converted the protein bands recognized by mab KD11 into forms with identical molecular weights.

This set of experiments determined how many enzymatic activities are involved in transferring PSA to its acceptor molecule NCAM. CHO cells, which are positive for NCAM and PSA (FIG. 1a), were used to perform a complementation analysis. After chemical treatment, PSA deficient CHO mutants were negatively selected by panning (B. Seed and A. Aruffo, Proc. Natl. Acad. Sci. USA 84: 3365–3369 (1987)) on the PSA specific monoclonal antibody 735 (M. Frosch et al., supra). All mutants positive for NCAM surface expression and α-2,3-sialylation (FIG. 1b) were subsequently used in fusion experiments. Surprisingly, only one complementation class (PST-C1) could be identified, with 40 individual clones selected from 9 independent mutagenesis experiments. In order to rule out the possibility that the mutation introduced in these clones is of a dominant phenotype, control fusions were carried out between the PST-C1 clone CHO-2A10 and either CHO-wild-type (CHO-wt) cells or the clone CHO-1E3 which is defective in sialic acid transport and therefore does not express sialylated proteins. In hybrid cells from both fusions, PSA-surface expression was detectable (FIG. 1a). These data strongly suggest that the polycondensation of α-2,8-linked sialic acids in mammals is mediated by a single enzyme, which is mutated in clones of the complementation class PST-C1.

EXAMPLE 2

In order to isolate the defective gene that is in PST-C1 clones, the mutant clone CHO-2A10 was used for expression cloning. Samples of CHO-2A10 cells were transfected, via electroporation, with a complementary DNA (cDNA) library prepared from RNA obtained from CHO-wt cells (in pCDM8) and vector pPSVE1-PyE carrying the polyoma large T-antigen (M. F. A. Bierhuizen et al., Genes Dev. 7: 468–478 (1993)). PSA-positive transfectants were collected by panning (B. Seed and A. Aruffo, supra) on mAb 735, and plasmid DNA was subsequently extracted and amplified in E. coli. MC1061/p3 following Seed et al, supra. After 3 cycles of transfection and panning, the cDNA encoding PST was enriched to about $1:10^3$ and could be finally isolated by sibling selection. The cDNA clone pEPST-ME7 (for eukaryotic polysialyl transferase clone ME7) was isolated.

pEPST-ME7 contained an insert of 2026 base pairs (bp) and an open reading frame of 1080 bp (SEQ ID NO: 1), potentially encoding a protein of 359 amino acids with a predicted Mr of 41.2 kDa. The amino acid sequence (SEQ ID NO: 2) showed the characteristic features of the sialyltransferase family, including the two sialylmotifs (K. Drickamer, Glycobiol. 3: 2–3 (1993)), as found at amino acids 141 to 183 and 258 to 300. The requirements of a type II transmembrane protein (P. Klein et al., Biochem. Biophys. Acta 815: 468–471 (1985)) are only partially fulfilled, however. A stretch of 13 hydrophobic amino acids (at least 16 are required) was found within the N-terminal domain of the molecule. These are amino acids 8 to 20 of SEQ ID NO: 2. Nevertheless, it is likely that this truncated hydrophobic motif represents a Golgi-retention-signal, since the cationic borders characteristic of type II transmembrane proteins were also found.

A vector which contains SEQ ID NO: 1 (pME7/PST-1) was deposited under the Budapest Treaty on 15 December 1994 at Deutsche Sammlung von Mikroorganismen und Zellkulturen GmbH (DSM), Mascheroder Weg 1b, D-38124 Braunschweig and was accorded the Accession Number DSM 9582. Comparison of the deduced PST primary sequence with the primary sequences of known sialyl transferases revealed that the similarity is predominantly concentrated to the sialylmotifs L and S (K. Drickamer, Glycobiol. 3: 2–3 (1993)). Analysis according to Higgins and Scharp, supra, yielded a dendrogram. The highest degree of homology is found with STX (59%), a sialyl transferase (H. Kitagawa et al, J. Biol. Chem. 269: 17872–17878 (1994)) and with the recently cloned GD3 synthase (28%), the only α-2,8-sialyltransferase identified so far (K. Nara et al., Proc. Natl. Acad. Sci. USA 91: 7952–7956 (1994), K. Sasaki et al., J. Biol. Chem. 269: 15950–15956 (1994)).

EXAMPLE 3

Transient expression of pEPST-ME7 CDNA in the mutant clone CHO-2A10, in an NCAM-positive subline of NIH-3T3, and in a COS-M6 clone stably transfected with human NCAM-140, i.e., DNA encoding human NCAM protein (COS-hN-6), respectively, resulted in surface expression of PSA. As shown in FIG. 2, PSA was attached to NCAM immunoprecipitated by anti-NCAM serum after expression of pEPST-ME7 in cell lines with the phenotype NCAM+/PSA−.

In standard Northern blot analysis, a PST specific cDNA probe recognized two bands of about 2.8 kb and about 5.1 kb in CHO-wt cells, and in both embryonic, and adult mouse brain (FIG. 3a; lanes 2–4). However, according to the restricted expression of PSA, both signals are drastically reduced in adult mouse brain. NIH-3T3 cells, which are negative for PSA, gave no hybridization signal (lane 1). These results imply that PST activity is regulated at the transcriptional level.

Recently, it has been shown that differential expression of PSA in sublines of the small cell lung cancer cell line HTB119 modulates potential malignancy (E. P. Scheidegger et al., J. Lab. Invest. 70: 95–106 (1994)). The expression of PST was investigated in clonal sublines derived from this tumor cell line. By limiting dilution, 3 sublines were obtained which, although identical in NCAM expression, varied in the amount of PSA present. In FACS analysis 100% of the cells in subline HTB119-54.2, 30% in subline HTB119-38, and only 2% in subline HTB119-45 were positive with mAb 735 (FIG. 3b). Poly (A)+ RNA from these cell lines was isolated and analyzed in Northern blot with a probe containing the entire coding region of pEPST-ME7. The results are shown in FIG. 3a (lanes 5–7). At least 6 bands were stained in highly polysialylated HTB119-54.2 and in HTB119-38 which express low amounts of PSA. Again, an extremely good correlation between surface expression and the level of PST mRNA was observed. These data suggest that PST is the cellular control element regulating PSA synthesis and furthermore indicate that the metastatic efficiency of these cells might be influenced by the abundance of PST mRNA.

Southern blot analysis of hamster and mouse genomic DNA using the PST cDNA as a probe, revealed a restriction pattern for the PST gene consistent with the presence of a single copy of the gene.

EXAMPLE 4

Preparation of Antisense DNA

The fact that PSA can affect the metastatic potential of tumors suggests the desirability of modulating synthesis of the molecule by regulating PST expression. This approach is seen as being useful as a method for treating pathological conditions, such as tumor associated diseases characterized by excess or inappropriate expression of PST, and/or inappropriate level of PSA. Three sets of experiments were carried out to test the ability of antisense oligonucleotides to inhibit expression of PST, and hence of PSA activity.

First, phosphorothioate oligonucleotide molecules complementary to nucleotide sequences of SEQ ID NO: 1 were synthesized with phosphorothioate linkages on an automated nucleotide sequencer following M. Matsukara et al., Proc. Natl. Acad. Sci. USA 84: 7705–7710 (1987). As a control, random oligonucleotide molecules having the same length were prepared in identical fashion. The purity of oligonucleotide molecules was determined by electrophoresis through 15% polyacrylamide gels stained with ethidium bromide.

The oligonucleotide molecules prepared are complementary to sequence sections of SEQ ID NO: 1 as follows:

Oligo 1 : Oligonucleotides 325–345 (21mer) (SEQ ID NO: 3)
Oligo 2 : Oligonucleotides 522–539 (18mer) (SEQ ID NO: 4)
Oligo 3 : Oligonucleotides 846–862 (17mer) (SEQ ID NO: 5)
Oligo 4 : Oligonucleotides 1356–1373 (18mer) (SEQ ID NO: 6)

PSA-positive CHO-wt cells were incubated with 3 μmol of each of the oligonucleotides. PSA activity was measured in a kinetic test, since PSA has a half-life longer than 24 hours. Cells were analyzed by FACS analysis with mAb 735 according to Example 3 after 20, 40, 60 and 80 hours.

In further experiments, the oligodeoxynucleotides, and polylysine modified conjugates were prepared according to J. P. Leonetti et al., Gene 72 (1988) 232–332, incorporated by reference, but summarized herein.

First, a solution of $N^6$, 2'-(3')o-dibenzoyl-5'-dimethoxytrityl-adenosine (2.15 g, 2.76 mmol) (Kempe et al., Nucleic Acids Res. 10 (1982) 6695–6714) and dimethylamino-4-pyridine (0.506 g, 4.15 mmol) in methylene chloride (12.3 ml) were combined with succinic anhydride (0.415 mmol) and triethylamine (0.58 ml, 4.15 mmol). The mixture was stirred for 2.5 hours, poured into 1M aqueous triethylammonium hydrogen carbonate (120 ml), and the resulting products were extracted with methylene chloride (3×150 ml). The combined organic layers were washed with water, dried over anhydrous sodium sulfate and evaporated to dryness. The residue was fractionated by silica gel chromatography using methanol-triethylamine-methylene chloride (0:1:99 to 2:1:97, v/v/v) as eluent. Fractions containing the pure-o-hemisuccinate were combined and evaporated to dryness. The residue was dissolved in 1.2-dimethoxyethane, pentachlorophenol (0.783 g, 2.94 mmol), followed by addition of N,N'-dicyclohexylcarbodimide (0.606 g, 2.94 mmol). The solution was stirred for 24 hours and evaporated to dryness. The resulting residue was purified by silica gel chromatography using acetone-methylene chloride (5.95 to 8.92, v/v) as eluent. Fractions containing pure succinate diester were combined and evaporated to dryness. Precipitation of the residue from petroleum ether resulted in a colorless powder (1.69 g) at a yield of 56%.

Long-chain alkylamine controlled pore glass (5 g from Sigma) was activated with triethylamine (0.3 ml, 1.5 mmol) in pyridine (10.5 ml). After evaporation of the solvent, the residue was suspended in a solution of succinate diester (1.69 g, 2.5 mmol) in dry pyridine (15 ml). After the mixture was stirred gently for 3 days at room temperature, the solid material was collected by suction, washed thoroughly with pyridine and methylene chloride, and dried. The glass beads were suspended in a capping solution 24 mol) made from acetic anhydride (0.186 ml), 19.98 mmol), 2.6-lutidine (0.198 ml, 1.71 mmol) and 4-dimethylaminopyridine (1.8 g, 14.7 mmol) in anhydrous tetrahydrofuran (30 ml). The mixture was stirred for 10 min. and the glass beads were collected by suction, washed with tetrahydrofuran (2×20 ml) and methylene chloride (4×20 ml) and then dried. Spectrophotometric measurement of the amount of dimethoxytrityl cation liberated by treating a portion of the functionalized adenosine-derivatized glass beads with 0.1M toluenesulfonic acid in acetonitrile indicated a loading of 24 μmol g.

(β)-Anomeric oligonucleotides, i.e., SEQ ID NOS: 3–6, were synthesized on a Biosearch Cyclone DNA synthesizer using the well known phosphoramide method. The synthesis was carried out on an adenosine derivatized support prepared as described supra. Samples of (β)-anomeric oligos (80 nmol) in 100 μm, of 20 mM Na acetate (pH 4.4) were oxidized with 4.6 μmol Na metaperiodate for 30 minutes at 0° C. in the dark. An equal volume of polylysine (PLL) (mean 14-kDa, Sigma) 80 nmol in 2M NaCl, 0.2M Na borate buffer (pH 8.4) and 100 μmol sodium cyanoborohydride were added. The mixture was incubated overnight at 20° C. and then loaded on Sephadex G-50 column equilibrated with 0.5M NaCL, 20 mM Na acetate buffer (pH 6.0). Each fraction was assayed for its oligo-PLL content by absorbance at 260 nm and by the BCA protein assay (from Pierce). The conjugates were stored at −80° C.

PSA positive CHO-wt cells were incubated with 0.9 μg oligo-PLL conjugate, and activity was measured as above.

In a third set of experiments, 3'-cholesterol-modified oligo-deoxynucleotides were prepared according to Chou, J. H. et al., Cancer Research 54 (1994) 5783–5787 and Reed, M. W., et al., Bioconjugate Chem. 2 (1991) 217–225, both of which are incorporated by reference.

Cholesterol-modified CPG (controlled pore glass) was used as support. The oligonucleotides were prepared from 2 μmol columns of these supports on an Applied Biosystems Model 394 DNA Synthesizer using the 1 pmol protocol supplied by the manufacture. 3'-cholesterol-modified oligonucleotides with $C_6$-linker were prepared from a commercially available 1 μmol CPG column (Clontech, Palo Alto, Calif.). Standard reagents for β-cyanoethylphosphoramidite coupling chemistry were used. After ammonia deprotection, the oligonucleotides were HPLC-purified, detritylated and precipitated from butanol as described in Reed, M. W., et al., supra. The oligonucleotides were at least 90% pure (HPLC).

PSA-positive CHO-wt cells (10,000/well) were plated in 24-well plates and incubated with 3 μmol oligonucleotide per well in 0.5 ml culture medium, and analyzed as above.

EXAMPLE 5

Recombinant Expression of Fusion-Free PST in *Escherichia Coli*

The DNA sequence coding for PST is modified in a way which allows for efficient expression in *E. coli*.

For expression, an expression plasmid is transfected into a suitable *E. coli* strain using standard methodologies. Such strains are, in the case of the use of an expression plasmid under the control of lac repressor such as the expression plasmid p11379, strains which possess a sufficiently high intracellular concentration of lac repressor. These kinds of strains can be prepared by transfection of a second plasmid such as pREP4 (Diagen GmbH), pUBS 500 or pUBS520 (Brinckmann et al., Gene 85 109–114 (1989)). The *E. coli* strains employed should preferably have low protease activity, as is the case, for instance, with *E. coli* UT5600 (Earhart et al., FEMS Microbiol. Lett. 6: 277–280 (1979)), *E. coli* BL21 (Grodberg and Dunn, J. Bacteriol. 170: 1245–1253 (1988)) or *E. coli* B. Expression cultivation is accomplished in a fashion according to the state of the art. For recovery, PST obtained as a protein aggregate from *E. coli* is processed, e.g., according to the procedures described in EP 0 241 022, EP 0 364 926, EP 0 219 874 and DE-A 40 37 196 all of which are incorporated by reference. An example of such a protocol is set forth.

PST-containing protein aggregates from *E. coli* fermentation (so called "inclusion bodies") are solubilized in 6M guanidinium hydrochloride, 100 mM Tris-HCl at pH 8, 1 mM EDTA, subsequently adjusted to a pH of 3 to 4 and dialyzed against 4M guanidinium hydrochloride at pH 3.5. The renaturing of the solubilized protein is then carried out in 1M arginine at pH 8, 1 mM EDTA, 5 mM GSH (glutathione, reduced) and 0.5 mM GSSG (glutathione, oxidized). From the renaturing preparation, PST can be obtained, for instance, after addition of 1.4M ammonium sulfate by adsorption to hydrophobic gel matrices such as Fractogel TSK Butyl and subsequent elution in 20 mM TrisHCl at pH 7.

EXAMPLE 6

Recombinant Expression of PST in Mammalian Cells

In order for recombinant PST to be expressed in heterologous mammalian cells, DNA from a first mammalian species which encodes a PST is ligated into a vector and is then transcribed in cells of a second mammalian species. This approach is used, e.g., to produce human PST in CHO cells, although it should be understood that a coding sequence from a mammalian species can also be transfected into cells of the same species. A strong promoter-enhancer system can be used, and in the case of genomic PST fragments, this step is required because the promoters of PST are active only in certain cell types (e.g. melanomas). Thus endogenous promoters may not be suitable for general recombinant expression in all cell types. Expression can also be accomplished by homologous recombination in vitro, whereby a suitable exogenous promoter is used in combination with a PST coding region. Such exogenous promoters and enhancers are generally from viruses such as SV40, hCMV, polyoma, or retroviruses. Alternatively, one can use promoter enhancer systems which are specific to a certain cell type or tissue type, such as WAP- or immune globulin promoters, or systems which are inducible, such as metallothionein and MMTV promoters. These constructs supplement the PST cDNA with donor and acceptor signals for RNA processing as well as a signal for poly-A-addition. For example, pCMX-pL1 (Umesono et al., Cell 65: 1255–1266 (1991)) is a suitable vector containing a CMV promoter. The PST cDNA is provided with EcoRI linkers and then ligated into the vector's single EcoRI cleavage site and, by using the other known cleavage sites in the polylinker of this vector, the PST cDNA is oriented in the proper reading frame for promotion of expression by the CMV promoter. An analogous procedure is applied when cloning into other vectors, such as pCDNA3 (Invitrogen, San Diego/USA) or pSG5 (Stratagene, Lajolla/USA). The DNA of these expression plasmids is from *E. coli* and may be transfected into a mammalian cell sample of choice, applying standard techniques. See, e.g. Methods of Enzymology 185 (Gene Expression Technology), ed. David V. Goeddel, Academic Press 1991, section V. After transfection, the cells may be cultured in minimum essential medium (MEM) without addition of fetal calf serum, whereby PST is detectible in the cell culture supernatant after 48 hours.

An example of such a system is the expression of pEPST-ME7 cDNA in the mutant clone CHO-2A10, in NCAM-positive subclones of NIH-3T3 cells, and in COS-hN-6. In each case surface expression of PSA was shown by immunofluorescence using mAb 735 as is now explained. The presence of PSA in these cells indicates that PST is being expressed, because the cells normally do not produce PSA.

Tissue culture dishes were seeded with freshly trypsinized cells 18 hours before transfection with 2 mg of pEPST-ME7, or an equal amount of the base vector pCDM8 described supra, using lipofectamin (Gibco BRL). 62 hours later, transfected cells were incubated with the PSA specific mab 735 for 30 minutes at room temperature, and any mab bound to target was detected with fluorescein conjugated, anti-mouse Fab fragments.

EXAMPLE 7

Digoxigenin(DIG)-Labelled RNA Probes

For preparing a probe, a nucleic acid fragment to be employed for hybridization is cloned in a suitable transcription vector (with a T3, T7 or SP6 promoter). For labelling, 1 to 2 µg of the plasmid were linearized, purified by means of phenol/chloroform extraction and precipitated with ethanol. 1 to 2 µg DNA (dissolved in DEPC-treated $H_2O$), 2 µl 10×transcription buffer, 40 U RNA polymerase (T3, T7 or SP6), 2 µl NTP/DIG-UTP mixture (10 mM ATP, CTP, GTP; 6.5 mM UTP; 3.5 mM DIG-UTP) and 1 µl RNase inhibitor (20 U/µl) were augmented with $H_2O$ to a volume of 20 µl.

This preparation was incubated for two hours at 37° C. Subsequently the DNA is removed by the addition of 2 µl RNase-free DNase I (10 U/µl) and by further incubation for 15 minutes at 37° C. The reactions were stopped by adding 1 µl 0.5M EDTA (pH 8.0), and the synthesized RNA was precipitated with 0.1 vol. 3M sodium acetate (pH 5.2) and 2.5 vol. ethanol. The RNA was washed once with 70% ethanol, dried and then dissolved in 100 µl $H_2O$ (DEPC-treated). To determine labelling efficiency a dilution series of the labelled sample and of a labelled control RNA are fixed on a nylon membrane and subsequently developed with the anti-DIG-Fab-AP conjugate as described in Example 8, infra.

EXAMPLE 8

Hybridization

RNA or DNA immobilized on nylon membranes was hybridized with DIG-labelled RNA probes. Hybridization was carried out under identical conditions, except that lower hybridization temperatures were used for DNA-RNA hybridizations.

The membranes were first pre-hybridized in hybridizing buffer (50% formamide, 50 mM sodium phosphate pH 7.0, 7% SDS, 0.1% N-lauroylsarcosine, 5×SSC, 2% blocking reagent) for 1 to 2 hours (65° C. in the case of RNA—RNA and 50° C. in the case of DNA-RNA hybridizations). Hybridization with DIG-labelled probe was carried out for 16 to 90 hours and, at 65° C. and 50° C., respectively. Immediately beforehand, the probe was heated to 98° C. for 5 minutes and subsequently cooled on ice. After hybridization, the membrane was washed, twice for 5 minutes in 2×SSC, 0.1% SDS (at ambient temperature) and twice for 15 minutes in 0.1×SSC, 0.1% SDS (at 65° C.)

The detection of the hybridized probe was carried out applying the following procedure:

1. Wash in buffer 1 (150 mM NaCl, 100 mM maleic acid pH 7.5) for 2 minutes;
2. Saturate the membrane in buffer 2 (1% blocking reagent in buffer 1) for 30 to 60 minutes;
3. Incubate with anti-DIG-Fab-AP conjugate (1:10,000 diluted in buffer 2; 75 mU/ml) for 30 minutes;
4. Wash twice in buffer 1 with 0.3% Tween-20 for 15 minutes;
5. Wash in buffer 3 (100 mM NaCl, 100 mM Tris/HCl pH 9.5) for 2 minutes.

The membrane, together with the substrate solution (CSPD: [di-sodium-3-(4-methoxyspiro{1,2-dioxetane-3,2'-(5'-chloro)tricyc lo[3.3.1.13,7]decan}-4-yl) phenylphosphate] diluted at a ratio of 1:100 in buffer 3), was wrapped in plastic foil and incubated for 30 minutes at 37° C. Thereafter, the substrate solution was removed from the foil, the foil was sealed, and the signals detected by exposure to X-ray, and development on film. The optimum exposure times were between 30 minutes and 2 hours.

EXAMPLE 9

As a first step in isolating a coding sequence for human PST, an appropriate eukaryotic cell system was needed. COS and CHO cells are used, frequently, as recipients for eukaryotic DNA, and were tested to determine if they were appropriate.

Samples of both COS-1 cells, and CHO cells, were transfected with plasmid pHβA-NCAM. This plasmid encodes a transmembrane form of the neural cell adhesion molecule ("NCAM"), which has a molecular weight of about 140 kDa. See Dickson, et al., Cell 50: 1119–1130 (1987), incorporated by reference. Both before and after transfection, the recipient cells were tested in an indirect immunofluorescence assay for polysialic acid, using monoclonal antibody 735, which is specific for this molecule. See Frosch, et al., Proc. Natl. Acad. Sci. USA 82: 1194–1198 (1985), incorporated by reference. The results of the assay showed that CHO cells were an inappropriate choice, because they expressed PSA before transfection. In contrast, COS-1 cells were negative both before and after transfection. Thus, COS-1 cells were used in the experiments which follow.

EXAMPLE 10

A human fetal brain cDNA library (Invitrogen, San Diego, Calif.) (40 ug) constructed in plasmid pcDNAI was cotransfected into $2.4–10^7$ COS-1 cells, together with an equal amount of pHβA-NCAM, using lipofectamine.

Forty-eight hours later, cells were tested via fluorescence activated cell sorting, using mAb 735, described supra, following Hayrinen, et al., Mol. Immunol. 26: 523–529 (1989), incorporated by reference. This methodology permitted separation of "mAb 735 positive" cells.

Once the positives were isolated, plasmid DNA in the positive cells was itself isolated, following the classic procedure of Hirt, J. Mol. Biol. 26: 365–369 (1967), incorporated by reference. The isolated plasmids were then amplified in host bacteria MC 1061/P3, using both ampicillin and tetracycline. This was possible because starting plasmid pcDNAI contains supF suppressor tRNA, and thus confers resistance to both antibiotics. In contrast, the pHS-A-NCAM plasmid confers resistance to ampicillin, but not to tetracycline. In this assay, the isolated plasmids were divided into 23 plates, each plate containing about 500 colonies of the bacteria. Plasmid DNA was prepared from each plate. As a result, the procedure results in rescue of positive library clones, but not others.

The recovered plasmid DNA was transfected into COS-1 cells with pHβA-NCAM and then subjected to sibling selection, which is a standard technique, resulting in sequentially smaller, active pools, activity being determined in an immunoassay, using mAb 735, described supra, and mAb 1263, the latter of these being used only in the analysis following cloning. In this way, a single plasmid, i.e., "pcDNAI-PST" was identified which, upon expression in host cells resulted in the appearance of PSA on the host cell surface. The presence of PSA in COS-1 cells co-transfected with pcDNAI-PST and pHβA-NCAM was detected by immunostaining with monoclonal antibody 735, as shown in FIG. 4D. The staining with monoclonal antibody 735 was abolished by pretreatment with endo-N, which hydrolyzes PSA. This is shown in FIG. 4F.

In order to confirm that the NCAM molecule contains polysialic acid (PSA), HeLa cells were cotransfected, using lipofectamine, with pHβA-NCAM alone, or pHβA-NCAM and pcDNAI-PST, in the same manner described supra, on COS-1 cells. Following transfection and incubation, the HeLa cells were subjected to Western Blotting. To perform the blotting, the lysates obtained from 2–10$^6$ cells (untransfected parent or cotransfected cells), were subjected to SDS gel electrophoresis, transferred to nitrocellulose, and incubated with anti-NCAM antibody (Becton-Dickinson). As shown in FIG. 4G, lysates of untransfected HeLa cells showed only barely detectable cross-reactivity of an ~100-kDa protein with anti-NCAM antibody (lane 1). In contrast, lysates of HeLa cells co- transfected with pcDNAI-PST and pHβA-NCAM displayed multiple bands of immunoreactivity corresponding to species of 140 kDa and greater molecular mass (see smear in lane 2). Lysates of the co-transfected cells that were treated with endo-N prior to electrophoresis displayed a single sharp band of immunoreactivity corresponding to a 140-kDa protein. These results confirm that pcDNAI-PST encodes a protein involved in synthesis of PSA, and that the PSA is attached to NCAM.

EXAMPLE 11

In view of these results, the sequence of the insert in pcDNAI-PST was deduced, using the classic Sanger methodology (Sanger, et al., Proc. Natl. Acad. Sci. USA 74: 5463–5467 (1977)), and is presented as SEQ ID NO: 7. This insert contains an open reading frame which encodes a protein with predicted 359 amino acid residues, (SEQ ID NO: 8) and a deduced molecular mass of 41,279, or about 41–42 kDa.

A hydropathy plot was prepared from the deduced amino acid sequence, using well known techniques. When analyzed, the plot suggests type II transmembrane topology with a short cytoplasmic sequence at the —NH$_2$ terminus, followed by a transmembrane domain, a so-called stem region, and a large catalytic domain, which one presumes resides in the Golgi lumen. This structure appears to be in agreement with all mammalian glycotransferases cloned thus far (see Schacter, in Fukuda, ed. Molecular Glycobiology Oxford University Press, 1994, pp. 88–162).

Analysis of the deduced amino acid sequence (SEQ ID NO: 8), shows 27.0% identity with GD3 synthase, an α-2, 8 sialytransferase (Nara, et al., supra; Sasaki, et al., supra) and 58.2% with "STX", an enzyme of unknown specificity (Kitagawa, et al., supra). There is also much less homology (9.7%) with Galβ1→3GalNAc α-2,3-sialyltransferase, taught by Lee, et al., Eur. J. Biochem. 216: 377–385 (1993).

Moving to a more in depth comparison, the highest degree of homology is found in a portion of the catalytic domain, the sialyl motif "L", (amino acids 141 to 185 in SEQ ID NO: 8) shared by all sialyl transferases cloned to date (Sasaki, et al, supra; Wen, et al., J. Biol. Chem. 267: 21011–21019 (1992); Datta, et al., J. Biol. Chem. 270: 1497–1500 (1995). Datta, et al., identify this motif as being the binding site for enzyme substrate CMP-NeuNAc. The predicted sialyl motif "S" is located at amino acids 288–300 in SEQ ID NO: 8.

Upstream from motif L, the predicted amino acid sequence shows a cluster of basic amino acids (Arg Arg Arg), at residues 114–116, and one at residues 137–140, i.e., Arg Arg Phe Lys. These clusters are either completely absent or incomplete in the corresponding sequences of GD3 synthase and STX. These basic amino acid clusters in PST may be critical for PST's binding to the acceptor containing multiple negatively charged sialic acid residues. A consensus sequence for polyadenylation was not found in the 3'-flanking sequence of the cloned cDNA; however, one can posit with some assurance that, during construction of the library, PST cDNA synthesis was started at a nucleotide sequence rich in adenine, i.e., nucleotides 1672–1682.

SEQ ID NO: 7

Sequence Size: 1894
Translation Position: 213–1292;
Genetic Code: Universal

```
          10        20        30        40        50        60        70        80
CGCAAACAGGGCGAGAGGTCGCTGGGCAGCGTTCGAGGACCAGAGGGAGCTCGGCCACAGAAGACCCCAGTGATCTGATC 90       100       110       120       130       140       150       160
CCGGGATCCCGGCTCCAAGCTCTCCTCGCATTTTACAGATTTCACCCCCGCGACTATCTCCCCAAAACGGAGCCTTTATA 170       180       190       200       210       220       230       240
TCAAGAGAAGGTGCGGGAGCTGGGGCAACCAGGACTTTCTCGGGCACCCAAGATGCGCTCCATTAGGAAGAGGTGGACGA
                                                       M  R  S  I  R  K  R  W  T  I 250       260       270       280       290       300       310       320
TCTCGACAATAAGTCTGCTCCTGATCTTTTATAAGACAAAAGAAATAGCAAGAACTGAGGAGCACCAGGAGACGCAACTC
  C  T  I  S  L  L  L  I  F  Y  K  T  K  E  I  A  R  T  E  E  H  Q  E  T  Q  L 330       340       350       360       370       380       390       400
ATCGGAGATGGTGAATTGTCTTTGAGTCGGTCACTTGTCAATAGCTCTGATAAAATCATTCGAAAGGCTGGCTCTTCAAT
  I  G  D  G  E  L  S  L  S  R  S  L  V  N  S  S  D  K  I  I  R  K  A  G  S  S  I 410       420       430       440       450       460       470       480
CTTCCAGCACAATGTAGAAGGTTGGAAAATCAATTCCTCTTTGGTCCTAGAGATAAGGAAGAACATACTTCGTTTCTTAG
  F  Q  H  N  V  E  G  W  K  I  N  S  S  L  V  L  E  I  R  K  N  I  L  R  F  L  D 490       500       510       520       530       540       550       560
ATGCAGAACGAGATGTGTCAGTGGTCAAGAGCAGTTTTAAGCCTGGTGATGTCATACACTATGTGCTTGACAGGCGCCGG
  A  E  R  D  V  S  V  V  K  S  S  F  K  P  G  D  V  I  H  Y  V  L  D  R  R  R 570       580       590       600       610       620       630       640
ACACTAAACATTTCTCATGATCTACATAGCCTCCTACCTGAAGTTTCACCAATGAAGAATCGCAGGTTTAAGACCTGTGC
  T  L  N  I  S  H  D  L  H  S  L  L  P  E  V  S  P  M  K  N  R  R  F  K  T  C  A
```

```
                 650       660       670       680       690       700       710       720
         AGTTGTTGGAAATTCTGGCATTCTGTTAGACAGTGAATGTGGAAAGGAGATTGACAGTCACAATTTTGTAATAAGGTGTA
          V  V  G  N  S  G  I  L  L  D  S  E  C  G  K  E  I  D  S  H  N  F  V  I  R  C  N 730       740       750       760       770       780       790       800
         ATCTAGCTCCTGTGGTGGAGTTTGCTGCAGATGTGGGAACTAAATCAGATTTTATTACCATGAATCCATCAGTTGTACAA
          L  A  P  V  V  E  F  A  A  D  V  G  T  K  S  D  F  I  T  M  N  P  S  V  V  Q 810       820       830       840       850       860       870       880
         AGAGCATTTGGAGGCTTTCGAAATGAGAGTGACAGAGAAAAATTTGTGCATAGACTTTCCATGCTGAATGACAGTGTCCT
          R  A  F  G  G  F  R  N  E  S  D  R  E  K  F  V  H  R  L  S  M  L  N  D  S  V  L 890       900       910       920       930       940       950       960
         TTGGATTCCTGCTTTCATGGTCAAAGGAGGAGAGAAGCACGTGGAGTGGGTTAATGCATTAATCCTTAAGAATAAACTGA
          W  I  P  A  F  M  V  K  G  G  E  K  H  V  E  W  V  N  A  L  I  L  K  N  K  L  K 970       980       990       1000      1010      1020      1030      1040
         AAGTGCGAACTGCCTATCCGTCATTGAGACTTATTCATGCTGTCAGAGGTTACTGGCTGACCAACAAAGTTCCTATCAAA
          V  R  T  A  Y  P  S  L  R  L  I  H  A  V  R  G  Y  W  L  T  N  K  V  P  I  K 1050      1060      1070      1080      1090      1100      1110      1120
         AGACCCAGCACAGGTCTTCTCATGTATACACTTGCCACAAGATTCTGTGATGAAATTCACCTGTATGGATTCTGGCCCTT
          R  P  S  T  G  L  L  M  Y  T  L  A  T  R  F  C  D  E  I  H  L  Y  G  F  W  P  F 1130      1140      1150      1160      1170      1180      1190      1200
         CCCTAAGGATTTAAATGGAAAAGCGGTCAAATATCATTATTATGATGACTTAAAATATAGGTACTTTTCCAATGCAAGCC
          P  K  D  L  N  G  K  A  V  K  Y  H  Y  Y  D  D  L  K  Y  R  Y  F  S  N  A  S  P 1210      1220      1230      1240      1250      1260      1270      1280
         CTCACAGAATGCCATTAGAATTCAAAACATTAAATGCTACATAATAGAGGAGCTCTAAAACTGACAACAGGAAAGTGT
          H  R  M  P  L  E  F  K  T  L  N  V  L  H  N  R  G  A  L  K  L  T  T  G  K  C 1290      1300      1310      1320      1330      1340      1350      1360
         GTAAAGCAATAAAGCACATTTTGAAACAAACAATATGCACTTCTTTTCTGAGATGCTTCCGAAGATTTGAAAATAGGATC
          V  K  Q  *

1370      1380      1390      1400      1410      1420      1430      1440
         CAAAACACGGCTGGGTTTCAGCATCCACCAATGAACTGAAAGGTGAATAAAGGACGTTCATGAGAAATCGACTACCAGCT 1450      1460      1470      1480      1490      1500      1510      1520
         GATGAAATACCTGCAAAGTGCTCTAAAAATTAAATATTTTGACTTTAAGGGTCCTAGTAAGTGCCACTTCCACTAAGAAT 1530      1540      1550      1560      1570      1580      1590      1600
         ACAGTTTGAATGTATAATCAGTAGTGTTTACAAGATCCAACAGTGCACTCATCATTAGTTAACAAAGCAAATATGTTCAT 1610      1620      1630      1640      1650      1660      1670      1680
         CACTGTCAGGCTGCCCACAGCAACACCAAGCATATTAGAAGAGGAACCCCAGGAACGCAACTCAGACCTTGGGAAATTAA 1690      1700      1710      1720      1730      1740      1750      1760
         ACCATCCTTGTCAGCAGAAGCCAAGATGGAAGCAGTTTGAGCAATGAAATCCGTAAGATTAAACAACTCAAGTAAATGCT 1770      1780      1790      1800      1810      1820      1830      1840
         TCAGTCAGGACTCTGAGTCTGATCATGAATTTTATGTTTTAATTTATGTTTTTTTTTTGTCTTCTGGAATCTCTTTTGG 1850      1860      1870      1880      1890
         TTTGGATATTGGGATGCTTAGAAATCCTTTCTGAGATGCATATGAGTGAGGAAA
```

SEQ ID NO: 8

Sequence Size: 1080
Translation Position: 1–1080;
Genetic Code: Universal

```
                 10        20        30        40        50        60        70        80
         ATGCGCTCCATTAGGAAGAGGTGGACGATCTGCACAATAAGTCTGCTCCTGATCTTTTATAAGACAAAAGAAATAGCAAG
          M  R  S  I  R  K  R  W  T  I  C  T  I  S  L  L  L  I  F  Y  K  T  K  E  I  A  R 90        100       110       120       130       140       150       160
         AACTGAGGAGCACCAGGAGACGCAACTCATCGGAGATGGTGAATTGTCTTTGAGTCGGTCACTTGTCAATAGCTCTGATA
          T  E  E  H  Q  E  T  Q  L  I  G  D  G  E  L  S  L  S  R  S  L  V  N  S  S  D  K 170       180       190       200       210       220       230       240
         AAATCATTCGAAAGGCTGGCTCTTCAATCTTCCAGCACAATGTAGAAGGTTGGAAAATCAATTCCTCTTTGGTCCTAGAG
           I  I  R  K  A  G  S  S  I  F  Q  H  N  V  E  G  W  K  I  N  S  S  L  V  L  E 250       260       270       280       290       300       310       320
         ATAAGGAAGAACATACTTCGTTTCTTAGATGCAGAACGAGATGTGTCAGTGGTCAAGAGCAGTTTTAAGCCTGGTGATGT
          I  R  K  N  I  L  R  F  L  D  A  E  R  D  V  S  V  V  K  S  S  F  K  P  G  D  V 330       340       350       360       370       380       390       400
         CATACACTATGTGCTTGACAGGCGCCGGACACTAAACATTTCTCATGATCTACATAGCCTCCTACCTGAAGTTTCACCAA
          I  H  Y  V  L  D  R  R  R  T  L  N  I  S  H  D  L  H  S  L  L  P  E  V  S  P  M
```

```
       410        420        430        440        450        460        470        480
TGAAGAATCGCAGGTTTAAGACCTGTGCAGTTGTTGGAAATTCTGGCATTCTGTTAGACAGTGAATGTGGAAAGGAGATT
  K  N  R  R  F  K  T  C  A  V  V  G  N  S  G  I  L  L  D  S  E  C  G  K  E  I 490        500        510        520        530        540        550        560
GACAGTCACAATTTTGTAATAAGGTGTAATCTAGCTCCTGTGGTGGAGTTTGCTGCAGATGTGGGAACTAAATCAGATTT
  D  S  H  N  F  V  I  R  C  N  L  A  P  V  V  E  F  A  A  D  V  G  T  K  S  D  F 570        580        590        600        610        620        630        640
TATTACCATGAATCCATCAGTTGTACAAAGAGCATTTGGAGGCTTTCGAAATGAGAGTGACAGAGAAAAATTTGTGCATA
  I  T  M  N  P  S  V  V  Q  R  A  F  G  G  F  R  N  E  S  D  R  E  K  F  V  H  R 650        660        670        680        690        700        710        720
GACTTTCCATGCTGAATGACAGTGTCCTTTGGATTCCTGCTTTCATGGTCAAAGGAGGAGAGAAGCACGTGGAGTGGGTT
  L  S  M  L  N  D  S  V  L  W  I  P  A  F  M  V  K  G  G  E  K  H  V  E  W  V 730        740        750        760        770        780        790        800
AATGCATTAATCCTTAAGAATAAACTGAAAGTGCGAACTGCCTATCCGTCATTGAGACTTATTCATGCTGTCAGAGGTTA
  N  A  L  I  L  K  N  K  L  K  V  R  T  A  Y  P  S  L  R  L  I  H  A  V  R  G  Y 810        820        830        840        850        860        870        880
CTGGCTGACCAACAAAGTTCCTATCAAAAGACCCAGCACAGGTCTTCTCATGTATACACTTGCCACAAGATTCTGTGATG
  W  L  T  N  K  V  P  I  K  R  P  S  T  G  L  L  M  Y  T  L  A  T  R  F  C  D  E 890        900        910        920        930        940        950        960
AAATTCACCTGTATGGATTCTGGCCCTTCCCTAAGGATTTAAATGGAAAAGCGGTCAAATATCATTATTATGATGACTTA
  I  H  L  Y  G  F  W  P  F  P  K  D  L  N  G  K  A  V  K  Y  H  Y  Y  D  D  L 970        980        990        1000       1010       1020       1030       1040
AAATATAGGTACTTTTCCAATGCAAGCCCTCACAGAATGCCATTAGAATTCAAAACATTAAATGTGCTACATAATAGAGG
  K  Y  R  Y  F  S  N  A  S  P  H  R  M  P  L  E  F  K  T  L  N  V  L  H  N  R  G 1050       1060       1070       1080
AGCTCTAAAACTGACAACAGGAAAGTGTGTAAAGCAATAA
  A  L  K  L  T  T  G  K  C  V  K  Q  *
```

EXAMPLE 12

The distribution of PST mRNA in human tissues was determined via Northern Blotting.

Human fetal and adult brain poly(A)+ RNA was obtained, and electrophoresed in 1.2% agarose gel containing 2.2M formaldehyde, followed by transfer to a nylon filter. Similarly, Northern blots of human multiple tissue poly(A)+ RNAs were purchased (Clontech, Palo Alto Calif.). The RNAs were hybridized with a gel purified CDNA insert of pcDNAI-PST, which had been labelled with $\alpha[^{32}P]$-dCTP via random oligonucleotide priming (Feinberg, et al., Anal. Biochem. 132: 6–13 (1983)), in accordance with Bierhuizen, et al., Genes and Dev. 7: 468–478 (1993).

Results, set forth in FIG. 5 show a strong, 6.5 kb band and a weak, 3.7 kb band in poly(A)+ RNA from fetal brain. The size difference is probably due to alternative usage of polyadenylation sites.

When compared to fetal brain, the signal in adult brain was weaker. The signal from fetal lung and fetal kidney was strong, while the fetal liver signal was not. With respect to adult tissues, PST transcripts were detected strongly in heart, spleen, and thymus tissue, and moderately in brain, placenta, lung, large intestine, small intestine, and peripheral blood leukocytes.

Different parts of adult human brain showed differing albeit weak levels of expression. Substantial amounts of PST mRNA were found in thalamus, subthalamic nucleus, substantia nigra, and cerebral cortex, with moderate amounts in amygdala, caudate nucleus, corpus callosum, hippocampus, and putamen. Generally, PST was expressed more in forebrain derivatives than in midbrain, hindbrain, and caudal neural tube derivatives.

EXAMPLE 13

In order to determine whether or not expression of PST mRNA is solely responsible for expression of polysialic acid, immunohistochemical analysis was carried out.

For these experiments, samples of tissue were fixed for 24 hours in cold, 4% paraformaldehyde in 0.1M phosphate buffer, (pH 7.4), followed by embedding in paraffin, and sectioning (3 um thickness).

Tissue sections were deparaffinized, hydrated, and then immersed in absolute methanol containing 0.3% $H_2O_2$ for 30 minutes.

Following this, mAb 735 described supra was used to determine presence of PSA, using the avidin-biotin-peroxidase methodology taught by Hsu, et al., J. Histochem. Cytochem. 29: 577–580 (1981). Briefly, biotinylated mAb 735 was contacted to the sections, followed by avidin-peroxidase complexes, and then a peroxidase substrate which yields a color upon reaction with the enzyme.

Figure 6A:
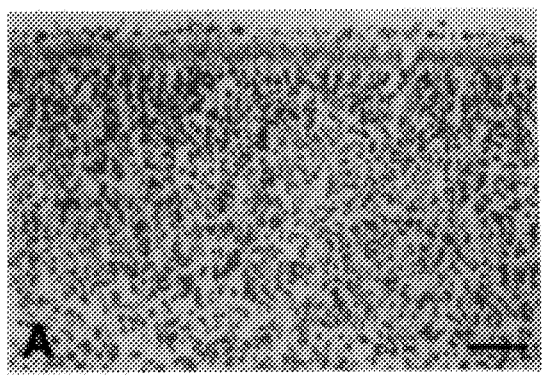
Figure 6B:
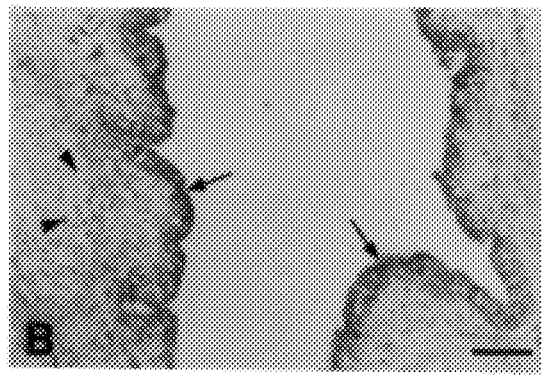
Figure 6C:
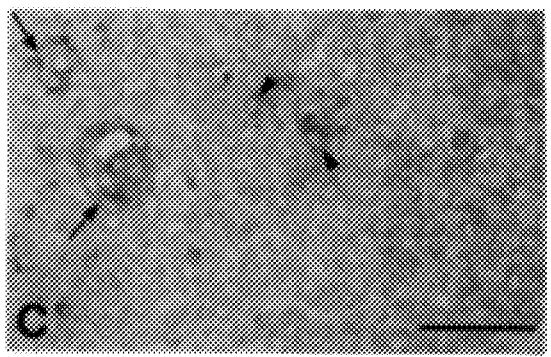
Figure 6D:
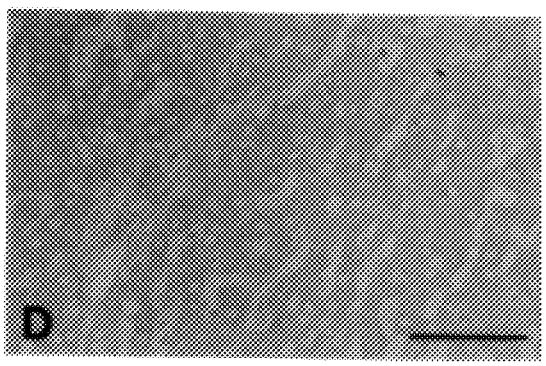

FIGS. 6A to 6D show strong presence of polysialic acid in neurons of fetal cerebral cortex, bronchial epithelia of fetal lung (arrows in FIG. 6B), Hassall's corpuscles of the thymus (see the arrows in FIG. 6C), and epithelial cells of the thymus (arrowheads in FIG. 6C). In contrast, tissues lacking PST mRNA were also negative for polysialic acid staining. These results suggest, strongly, that PST alone is responsible for biosynthesis of polysialic acid.

EXAMPLE 14

A study was carried out to determine what effect, if any, polysialic acid expression in living substrates had on neurite outgrowth. It has been reported that neural cell migration and axon outgrowth were influenced by polysialic acid expressed on either neural cells, or crude membrane substrates prepared from chick tectum. See Tang, et al., Neuron 13: 405–414 (1994). Doherty, et al., Neuron 5: 209–219 (1990); Boisseau, et al., Development 112: 69–82 (1991). In one of these studies (Doherty, et al), neurite outgrowth was observed in neural cells on substrate cultures of 3T3 cells which had been transfected to express NCAM. HeLa cells, cotransfected as described in Example 10, supra, were used as substrate for growth of sensory neurons from dorsal root ganglia of 10 day old chick embryos, and neurons from ventral portions of spinal cords from six day old chick embryos, which predominantly contained motor neurons. Prior work by Doherty, et al., Neuron 5: 209–219 (1990) has shown that both of these cell types express both NCAM and polysialic acid.

Cells were trypsinized (0.5% trypsin), counted, seeded at low density over monolayers of HeLa cells, and cultured in Dulbecco's modified Eagle's medium containing 10% fetal bovine serum. The sensory neuron culture had nerve growth factor added to it as well.

Cultures were grown up for 15 hours, after which they were fixed with 4% formaldehyde, in phosphate buffered saline. The fixed cells were then stained with anti neurofilament antibody RM 0270 (Lee, et al., J. Neurosci. 7: 3474–3488 (1987)), followed by fluorescein isothiocyanate conjugated mouse anti-IgG antibody. The length of the neurites were measured, using the standard "JAVA" morphometric system (Jandel Scientific), via epifluorescence. The longer neurite of each neuron was measured for 30 neurons within adjacent fields, in duplicate experiments. Only neurons whose neurites did not overlap others were included. Mean neurite lengths, and the number of neurite branches per neuron occurring on three different substrates (untransfected HeLa cells, those transfected by N-CAM cDNA, and cells transfected by both N-CAM cDNA, and PST cDNA), were counted, and compared by Student's T test.

Figure 7A:
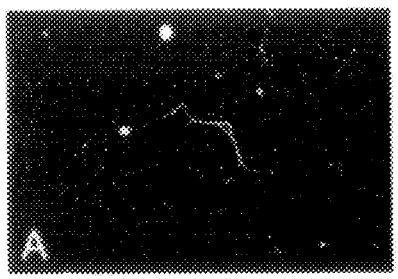
Figure 7B:
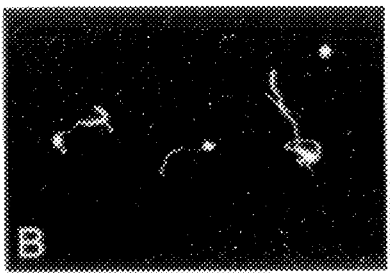
Figure 7C:
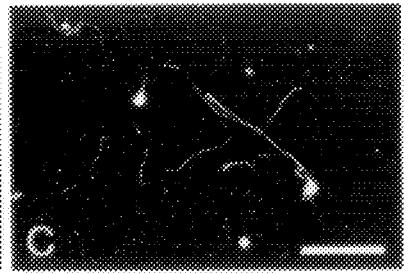
Figure 7D:
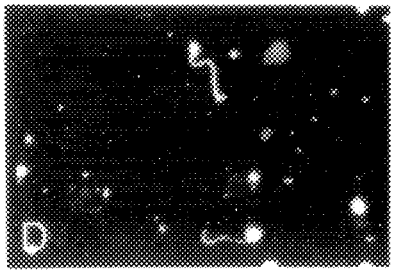
Figure 7E:
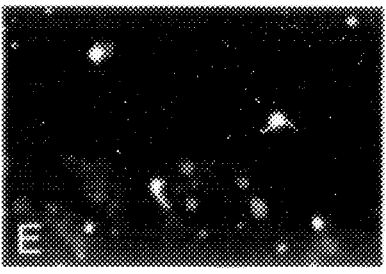
Figure 7F:
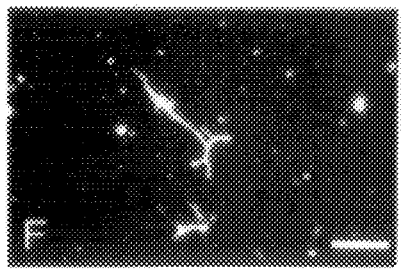

FIGS. 7A, B and C show these results. Those neurons derived from dorsal root ganglia (almost exclusively sensory neurons), showed modest neurite outgrowth on confluent layers of untransfected HeLa cells (mean length; 196.3 µm), as in FIG. 7A and HeLa cells expressing N-CAM (171.3 µm), as in FIG. 7B. Those cells cultured on the cotransfectants, however, grew neurites with a mean length of 253.6 µm. See FIG. 7C. The branching on these neurons (mean: 4.0 branches/neuron) was significantly higher than those grown on cells transfected with NCAM only (2.3 branches/neuron). The same pattern was found with the spinal cord derived neurons, which are mainly motor neurons (figure D, E and F).

The work set forth herein shows that polysialic acid is a critical regulator of neurite outgrowth on living cells.

EXAMPLE 15

Isolation of Nucleic Acids Encoding Mouse PST

1. Isolation of Mouse PST cDNA

To isolate nucleic acids encoding mouse PST, cDNAs were prepared using RNA isolated from neonatal brain of BALB/c mice as the template, following standard procedures. The cDNAs were subjected to nucleic acid amplification (performed according to standard procedures) using oligonucleotides based on the human PST cDNA (see Sequence ID NO: 7) as primers. Specifically, the first primer corresponded to nucleotides 206–225 in SEQ ID NO: 7 and the second primer corresponded to the complement of nucleotides 1284–1299 in SEQ ID NO: 7. The product of this amplification procedure, which is similar in length to the cDNA encoding human PST, is purified, ligated into a plasmid such as pBluescript II, and characterized by DNA sequence analysis.

2. Isolation of Genomic DNA Encoding Mouse PST

Genomic DNA was isolated from mouse cell line I29SVJ according to standard procedures and ligated into the Lambda FIX II cloning vector. The resulting genomic DNA library was screened using conditions as described supra for hybridization to an oligonucleotide probe corresponding to nucleotides 1–557 of SEQ ID NO: 7. Hybridizing plaques were purified and characterized by DNA sequence analysis. DNA sequence analysis of the genomic DNA thus isolated revealed that it contains at least two exons: one corresponding to an extreme 5'domain of the human PST cDNA (i.e., nucleotides 1–325 of SEQ ID NO: 7) and a second corresponding to a more downstream location of the human PST cDNA (i.e., nucleotides 458–715 of SEQ ID NO: 7). Through such analysis of the complete isolated DNA, the genomic structure of the gene encoding mouse PST can be elucidated. The resulting information is particularly useful in designing gene "knock-out" experiments in mice, wherein the mouse PST gene in mouse embryos is rendered nonfunctional. The resulting transgenic mice are then analyzed for the effects of a lack of PST activity.

EXAMPLE 16

PST is Capable of Catalyzing the Synthesis of in Vivo, in the Absence of N-CAM

The results set forth in examples 1–15 established that PST, when expressed together with N-CAM in cell lines such as HeLA, CHO-2A10, and NIH/3T3, results in the production of polysialic acid (PSA). To ascertain whether PST can catalyze synthesis of PSA in cells which do not express N-CAM, COS-1 cells were transiently transfected with cDNA encoding PST, without cotransfection with cDNA encoding an N-CAM substrate. Transfection was carried out using the plasmid pcDNAI-PST, described supra, using lipofectamine. After 48 hours, the transfected COS-1 cells were subjected to immunoflourescent staining, using murine monoclonal antibodies M6703 (Nakayama, et al, J. Histochem Cytochem 41:1563–1572 (1993)) 12E3 (Seki, et al. Anat. Embryol 184: 395–401 (1991)), and 735 (Frosch, et al, Proc. Natl. Acad. Sci. USA 82: 1194–1198 (1985)). All of these references are incorporated by reference. The mAb M6703 is known to react with oligosialic acids which contain 2 or 3 α-2,8 linked sialic acid residues, 12E3 reacts with polysialic acids containing 6 or more residues of α-2,8 linked sialic acid, and 735 with polysialic acids containing 8 or more of these residues.

Following staining with the murine mAbs, fluoresein isothiocyanate (FITC) conjugated goat-antimouse IgG antibody F(ab')$_2$ fragments were added to detect M6703 and 735, while FITC conjugated goat-antimouse IgM antibody F(ab')$_2$ fragments were used to detect 12E3. The IFA protocol was identical to that described supra.

The strongest staining pattern obtained was that using 12E3. These results indicate that the majority of PSAs formed by PST were those containing 6 or more α-2,8 linked sialic acid residues.

It was confirmed that N-CAM was absent, because there was no staining of the transfectants with an anti N-CAM antibody. Thus, PST does not require N-CAM in order to produce PSAs.

These results were confirmed, using HeLa as the host cell line. In these experiments, parallel experiments, HeLa cells were cotransfected with pcDNAI-PST and pSV$_2$neo, and selected with antibiotic G418, using standard protocols, i.e., those described in the prior examples. Following the selection, immunofluorescent staining was carried out in the same manner described for the COS-1 cells.

Transfected HeLa cells were stained with mAb 735. When the transfectants were treated with the enzyme endo- N, which is known to cleave PSA, no staining was detected by antibody 735. The data generated and described herein show that N-CAM is not required for production of PSA, when PST is present.

EXAMPLE 17

PST Adds PSA to Molecules Other Than N-CAM in Vitro: Construction of Vectors Encodina Fusion Proteins The data from the example 16 suggest that PST can add PSA to molecules other than N-CAM. A series of experiments were carried out to further demonstrate PSA synthesis via PST in vitro, beginning with the following.

A fusion protein was produced, using a putative catalytic domain for PST, a signal peptide, and an IgG binding domain. The signal peptide was derived from human granulocyte colony stimulating factor (G-CSF), and the IgG binding domain was that of the S. aureus protein A.

The fusion protein was prepared using cDNA sequences, and the well known polymerase chain reaction ("PCR" hereafter). The pcDNAI-PST plasmid was used as a template. The upstream and downstream primers used were:

5'-CGGGATCCGG GTGAATTGTC TTTGAGTCGG T-3' (SEQ ID NO:9)

and

5'-GGGGTACCTC AAAATGTGCT TTATTGCTTT ACAC-3' (SEQ ID NO:10).

IN SEQ ID NO:9, the underlined portion is a BamHI restriction site, while the underlined portion of SEQ ID NO:10 is a KpnI restriction site.

Following standard PCR techniques, the resulting product encompassed nucleotides 118 (codon 40) through 1092 (12 nucleotides downstream of the stop codon. Thus, amino acids 40–359 of SEQ ID NO:8 constitute a soluble, PST active molecule.

Parallel to this procedure, the plasmid pAMoA-GD3, described by Sasaki, et al., J. Biol. Chem 22:15950–15956, (1994) incorporated by reference, was digested with BamHI and KpnI, with the result that pAMoA was formed, which contained only DNA encoding the human G-CSF signal sequence and a sequence encoding S. aureus protein A.

The PCR product referred to herein was then digested with the same two endonucleases, and cloned into pAMoA, using standard methods. The resulting plasmid has been named pAMoA-PST.

The plasmid pAMoA-PST was then digested with SalI and Asp718, resulting in excision of cDNA encoding a fusion protein consisting of the human G-CSF signal peptide, S. aureus protein A, and the PST sequence referred to, supra. The released cDNA insert was filed in using Klenow fragment of DNA polymerase I, and cloned into pcDNAI which had been digested previously with EcoRV. The resulting plasmid was named pcDNAI-A PST. A control vector was also prepared, consisting of only signal peptide and protein A cDNA. This vector was named pcDNAI-A. Standard methodologies were used to confirm that the vectors were in proper 5'-3' orientation.

EXAMPLE 18

PST Adds Sialic Acid To Molecules Other Than N-CAM

The vectors pcDNAI-A PST and pcDNAI-A were transfected, separately, into COS-1 cells, using the lipofectamine method described, supra. The transfected cells were cultured for 62 hours, after which any fusion protein secreted into culture medium was adsorbed to IgG-Sepharose 6FF, essentially following the methods of Kukowska-Latallo, et al., Genes Dev 4: 1288–1303 (1990), and Bierhuizen, et al., Proc. Natl. Acad. Sci USA 89:9326–9330 (1992), both of which are incorporated by reference. Resin was collected via centrifugation, washed nine times with 50 mM Tris-HCl, pH7.5 containing 1% bovine serum albumin followed by two washes with 20 mM Tris-HCl, pH7.5, containing 7.5 mM $CaCl_2$, and 0.05% Tween 20. Finally, the resin was suspended in an equal volume of serum free medium opti-MEM1. This entire procedure is akin to that described by Kukowska-Latallo, et al., supra Sasaki, et al., J. Biol. Chem 22:15950–15956 (1994), incorporated by reference.

The enzyme activity of the fusion protein was tested [following Sasaki, et al., supra, and Kojima, et al., FEBS Lett 360:1–4 (1995), incorporated by reference]. Briefly, a substrate solution was prepared, which contained 100 λg of a substrate sialylated glycoprotein (elaborated upon infra), dissolved in 50µl of 0.1M sodium cacodylate buffer (pH 6.0), which contained 20 mM $MnCl_2$, 1% Triton CF-54, and 2.4 nmoles of CMP-[$^{14}$C] NeuNAc, which served as a donor substrate. An aliquot of 50 µl of the solution containing the fusion protein was added, mixed, and the resulting mixture was incubated at 37° C., for either 4 hours, or 24 hours. Following incubation, the reaction mixture was centrifuged. Samples (20 µl), of the resulting supernatant were mixed with 20 µl of the sample buffer for SDS-gel electrophoresis, described by Lemmli, Nature 227:680–685 (1970). These mixtures were heated at 85° C. for 3 minutes. The remaining sample was stored at −70° C. until used.

The products contained in the sample buffer were subjected to SDS polyacrylamide gel electrophoresis (7.5% acrylamide gel), and any sialic acids incorporated therein were determined fluorographically. The fluorography was carried out by fixing the gels in 40% methanol, for 30 minutes, followed by two 15 minute soaks in dimethylsulfoxide followed by soaking in dimethylsulfoxide containing 2,5 -diphenyloxazole (18.5 g in 88 ml of DMSO) in accordance with Bonner, et al., Eur. J. Biochem 46:83–88 (1974), incorporated by reference.

The sialylated glycoproteins referred to supra were rat $α_1$,—acid glycoprotein, fetuin, and human $α_1$,—acid glycoprotein, all of which had been purchased from Sigma.

In order to analyze the linkages of any incorporated sialic acids, 90% ethanol was added to the reaction mixtures, followed by centrifugation. The products were washed, once in 90% ethanol, and the samples were then digested with one of NANase I (0.17 units/ml), NANase II (5 units/ml), or NANase III (1.7 units/ml), all of which are commercially available. The digestion was at 37° C. for 19 hours, in accordance with the supplier's instructions. NANase I cleaves α-2,3 linked sialic acids. NANase II cleaves α-2,3 linked sialic acids as well as α-2,6 linked sialic acids. NANase III cleaves all of α-2,3 linked sialic acids, α-2,6 linked sialic acids, and α-2,8 linked sialic acids. Also, reaction mixtures were digested for 36 hours with either of N-Glycanase, following the manufacturer's instructions, or with endoneuraminidase ("endo-N"), in accordance with Hallenback, et al., J. Biol. Chem 262:3553–3561 (1987), incorporated by reference. Following digestion, the materials were subjected to SDS-polyacrylamide gel electrophoresis and fluorography, as described herein.

When fetuin was incubated for 24 hours in the manner described, a wide, high molecular weight band (100–170kd), was formed. While some small amounts of wide and high molecular weight bands were found for the two a acid glycoproteins, the majority of the radioactivity from the donor substrate moved very close to the position of untreated glycoproteins (≈48 kd for rat, and 44 kd for human).

The products formed by PST were not susceptible to NANase II digestion, but were digested by NANase III, which differs from NANase II in its ability to cleave α-2,8—linked sialic acid. Further, the products were susceptible to cleavage by both endoneuriminadase, and N-Glycanase.

The conclusion drawn from this is that the wide, high molecular weight bands represent glycoproteins containing polysialic acid side chains in N-Glycans. The digestion pattern with the NANases and N-Glycanase proves that the attachment was through α-2,8 linkages.

When fetuin product was treated with endo-N, it migrated at about 90 kd, which is larger than the untreated molecule. This can probably be attributed to the inability of endo-N to cleave polysialic acid chains which are shorter than 5 or 6 sialic acid residues in length, as was explained, supra. The product following endo-N treatment most likely represents fetuin containing polysialic acid chains consisting of 6 or fewer α-2,8 sialic acid residues in a side chain. Spiro, et al., J. Biol Chem 263: 18253–18268 (1988), show that fetuin contains both N- and O- linked oligosaccharides. Since N-Glycanase treatment removed almost all of the incorporated sialic acid, it can be concluded that polysialylation took place on N-glycans.

EXAMPLE 19

Requirements of a PST Acceptor

In a further set of experiments, investigations were carried out to determine what requirements had to be satisfied by a molecule for it to act as a PST acceptor. Since the previous example showed that fetuin did act as a PST acceptor, it was digested with various neuraminidases and with N-Glycanase, to yield a series of digestion products. These products were then used in acceptor experiments. Briefly, the fetuin was digested with NANase I, II, III or N-Glycanase, in the same manner as was described, supra. Following digestion, 90% ethanol was added to the mixture, mixed well, digested substrate was recovered by centrifugation, and washed with 90% ethanol. These products were desialylated (NANase treatment), or deglycosylated (N-Glycanase treatment). They were then used in precisely the same way that the rat $\alpha_1$- acid glycoproteins were used, supra. The results, show that once α-2,3-linked sialic acids were removed from fetuin, PST did not add sialic acid residues, whether or not α-2,6 linked sialic acid residues were present (see the two left most lanes of the figure). When N-glycans were removed, there was no incorporation either (see last lane from the left).

These studies confirm that PSA is attached to an α-2,3 linked sialic acid on a glycoconjugate template and that PST alone can add the first α-2,8 α linked sialic acid to a precursor containing α2,3- linked sialic acid and then add multiple α-2,8-linked sialic residues to the acceptor, yielding PSA. The experiment also established an in vitro assay system for PSA synthesis.

The foregoing examples set forth, as one aspect of the invention, isolated nucleic acid molecules which encode polysialic acid transferases. These transferases may be eukaryotic proteins, more preferably mammalian, and most preferably human. Among the non-human mammalian species embraced by the invention are various rodent species, such as mouse, rat, rabbit, and guinea pig "PSTs". Especially preferred are isolated nucleic acid molecules comprising or consisting essentially of SEQ ID NOS: 1 or 7, as well as their complementary sequences, as well as isolated nucleic acid molecules which encode proteins consisting of SEQ ID NO: 2 or SEQ ID NO: 8. Also preferred are isolated nucleic acid molecules consisting of nucleotides 301–1377 of SEQ ID NO: 1, and consisting of nucleotides 213–1289 of SEQ ID NO: 7. Also included are isolated nucleic acid molecules which (i) code for PST proteins as described herein and which hybridize with one or both nucleotides 721–1200 of SEQ ID NO: 1, and nucleotides 633 to 1112 of SEQ ID NO: 7 under stringent conditions. The term stringent conditions is discussed below.

Proteins such as those coded by the sequences set forth supra, and all isolated protein having PST activity are also a feature of the invention. These proteins may have particular amino acid sequences, such as that of SEQ ID NO: 2 or SEQ ID NO: 8. The PST proteins can occur in natural allelic variations which differ from individual to individual. Such variations of the amino acids are usually amino acid substitutions. However, they may also be deletions, insertions or additions of amino acids to the total sequence. The PST protein according to the invention—depending, both in respect of the extent and type, on the cell and cell type in which it is expressed—can be in glycosylated or non-glycosylated form.

The term "polysialyl transferase activity" denotes the protein's capability of catalyzing the polycondensation of α-2,8-linked sialic acids in vivo and/or in vitro. The number of sialic acids that are being condensed is dependent on the surrounding conditions, including, e.g., the cell type in which condensation takes place, and on the CMP-activated substrate (sialic acid or derivatives, e.g. N-glycolylneuraminic acid or N-acetylneuraminic acid). The number of condensed sialic acids may vary widely and ranges between but a few (e.g. 10) and several hundreds or thousands of such monomers. Preferably, N-acetylneuraminic acid residues are condensed. PST activity may also include induction of PSA synthesis in NCAM expressing cell lines as well as cell-free synthesis of oligosaccharides. Expression of PST in tumorigenic cells can influence metastatic efficiency of the cells, and expression of PST in substrate cells and/or nerve cells can also regulate neurite outgrowth, as was shown, supra.

The polysialyltransferases of the invention catalyze the polycondensation of sialic acids on acceptor structures like NCAM but do not use isolated poly- or oligomeric N-acetylneuraminic acid substrates like colominic acid or capsular polysaccharides from E.coli K1, E.coli K92 or Neisseria meningitidis sero group B. In contrast to this, the bacterial polysialyltransferases use such substrates from E.coli K1 (PST of C.Weisgerber et al., Glycobiol. 1 (1991) 357) E.coli K92 (PST of S. M. Steenbergen et al., J. Bacteriol. 174 (1992) 1099), or from Neisseria meningitidis sero group B (M. Frosch et al., Mol. Microbiol. 5 (1991) 1251). Therefore, the polysialyltransferases according to the invention show a different acceptor specificity than bacteria polysialylic transferases.

The term "do not use isolated poly- or oligomeric N-acetylneuraminic acid substrates" means that a conversion of these substrates cannot be observed within the detection limit in an appropriate detection method. Such methods of detection are well known to one skilled in the art and are described, for instance, in Cho and Troy, Proc. Natl. Acad. Sci. USA 91 (1994) 11427–11431.

"Isolated" and/or "purified" as used herein indicates that the material modified thereby has been modified from its native, in vivo cellular environment. As a result of this modification, the recombinant DNAs, RNAs, polypeptides and proteins of the invention are useful in ways that the DNAs, RNAs, polypeptides or proteins as they naturally occur are not, such as in the isolation of nucleic acids encoding related proteins and in the treatment of certain pathological conditions.

"Stringent conditions" as used herein, refers to hybridization in the presence of 1M NaCl, 1% SDS, and 10% dextran sulfate, followed by two washes of a filter at room temperature for 5 minutes, in 2×SSC, and one final wash for 30 minutes. This final wash may be at 0.5×SSC, 0.1% SDS, more preferably at 0.2×SSC, 0.1% SDS, and most preferably at 0.1×SSC, 0.1% SDS, final wash taking place at 65° C. Those of ordinary skill in the art will recognize that other conditions will afford the same degree of stringency, and are encompassed by the phraseology "under stringent conditions", and are encompassed herein.

With the aid of the nucleic acid molecules provided by the invention, and techniques well known to the skilled artisan, the PST gene or its variants in genomes of any mammalian cells and tissue, preferably in such cells or tissue which are positive for PSA may be isolated. Such processes and suitable standard stringent hybridization conditions are known to a person skilled in the art and are described for example by J. Sambrook, Molecular Cloning: A Laboratory Manual (1989) and B. D. Hames, et al., Nucleic Acid Hybridization: A Practical Approach (1985). In this case the standard protocols described in these publications are usually used for the experiments. In particular section IX of Hames, "Hybridization of radiolabeled probes to immobilized nucleic acid", page 947–962 with regard to the hybridization of nucleic acid molecules, and to section XI, page 1145–1161, "Conditions for hybridization of oligonucleotide probes" with regard to the hybridization of oligonucleotide probes, both quotations beings incorporated herein by reference. Standard stringent conditions are also described, for example, by Hotke and Kessler, "The Dig System User's Guide For Filter Hybridization" (1990).

Cells and t issue which are positive for PSA can be identified either by an antibody which is specific for polysialic acids and/or by the use of endoneuraminidase NE. Such specific antibodies can be easily produced according to M. Frosch et al., supra or according to Moolenaar, et al., supra, both of which are incorporated herein by reference. The isolation of endoneuraminidase NE is described in S. Tomlinson and P. W. Taylor, J. Virol. 55: 374–378 (1985), which is incorporated herein by reference. Endoneuraminidase NE degrades α-2,8-linked sialic acids with at least 8 sialic acid residues and releases in the cell or tissue supernatant monomeric sialic acids.

For the detection of these free neuraminic acids (sialic acids), an assay is described by L. Warren, J. Biol. Chem. 234: 1971–1975 (1959), which is incorporated herein by reference. With this thiobarbituric acid assay (TBA assay) free reducing ends (also oligomers as are obtained in the endoneuraminadase NE digest, 3 to 8 residues) are detectable.

Thus it is possible to detect polysialic acid in cells by harvesting the cells, washing in PBS, digesting with endoneuraminidase NE (in PBS), employing the supernatant with released sialic acid oligomers in the TBA assay and in the calorimetric detection.

For example, nucleic acids encoding mammalian proteins having PST activity may be isolated by screening suitable cDNA or genome libraries under suitable hybridization conditions with nucleic acids disclosed herein (including nucleic acids derived from any of SEQ ID NOS: 1 or 7). The library can be screened with a portion of the disclosed nucleic acids including substantially the entire coding sequence thereof or with a suitable oligonucleotide probe based on a portion of the nucleic acids. As used herein, a probe is a single-stranded DNA or RNA that has a sequence of nucleotides that includes at least about 10–50 contiguous bases, preferably 16–40, most preferably 25–30, that are the same as (or the complement of) any contiguous bases set forth in any of SEQ ID NOS: 1 or 7. Preferred regions from which to construct probes include sequences predicted to encode transmembrane domains, catalytic domains, sialyl-motifs and the like.

Either the full-length cDNA clones, fragments thereof or oligonucleotides based on portions of the cDNA clones can be used as probes, preferably labeled with suitable label means for ready detection. Non-radioactive labels are preferred. These probes can be used for identification and isolation of additional nucleic acids encoding proteins having PST activity.

Thus, in accordance with another embodiment of the present invention, there is provided a method for identifying nucleic acids encoding proteins having PST activity said method comprising: contacting mammalian DNA with a nucleic acid probe as described above, wherein said contacting is carried out under conditions favorable to the hybridization of the probe to its complement, and identifying nucleic acid molecules which hybridize to the probe.

After screening the library, positive clones are identified by detecting a hybridization signal; the identified clones are characterized by DNA sequence analysis and then examined by comparison with sequences set forth herein to ascertain whether they encode a complete PST protein. The cDNA clones can be incorporated into expression vectors and expressed in suitable host cell lines as described herein to determine if the corresponding protein product displays PST activity as also described herein.

Alternatively, nucleic acid amplification techniques which are well known to those of skill in the art, can be used to isolate nucleic acids encoding proteins with PST activity. This is encompassed by employing oligonucleotides based on the sequences disclosed herein in SEQ ID NOS: 1, or 7 as primers for amplifying mammalian RNA or DNA.

Once nucleic acid encoding a particular protein with PST activity has been isolated, ribonuclease (RNase) protection assays and in situ hybridization assays can be employed to determine which cells and tissues express mRNA encoding the protein. These assays provide a sensitive means for detecting and quantifying an RNA species in a complex mixture of total or cellular RNA.

The use of recombinant DNA technology enables the production of numerous PST protein derivatives. Such derivatives can for example be modified in individual or several amino acids by substitution, deletion or addition. The derivatization can for example be carried out by means of site directed mutagenesis. Such variations can be easily carried out by a person skilled in the art (J. Sambrook, supra, B. D. Hames, supra) . It merely has to be ensured that the characteristic properties of the PST protein (polysialyl transferase activity) are preserved.

As PST is an intracellular (Golgi-resident) enzyme which may be present in the cell in a dimeric form usually linked via the N-terminus, dimerization in the cell is essentially carried out via the transmembrane region (approximately amino acid Nos. 8 to 20 of SEQ ID NOS: 2 and 8, e.g.). Even when in monomeric form, however, the enzyme will display activity. A soluble enzyme which is monomeric and in which the transmembrane region and, thus, approximately the first 20 to 30 amino acids, preferably 25 amino acids, are absent, is preferred. A soluble enzyme of this type is also active in vitro and catalyzes the polycondensation of α-2,8-linked sialic acids.

The invention thus also comprises an isolated PST protein which is a product of prokaryotic or eukaryotic expression of an exogenous DNA as described herein.

The invention additionally concerns PST proteins and nucleic acid molecules from other cells and tissue such as mammalian cells and tissues, including mouse, rat, bovine, sheep, etc., which exhibit polysialyl transferase activity in an essentially analogous manner. These proteins can be obtained in a manner well known to the art. For example, given the nucleotide sequences disclosed herein, one screens a library, such as a cDNA library of a particular mammal or other eukaryote, for sequences which hybridize with the complements of disclosed sequences. These "targets" as it were presumably encode functional equivalents of the PST proteins encoded by the disclosed sequences. Transfection with these isolated targets is expected to lead to expression of the PST protein.

With the aid of the nucleic acid molecules of the invention, the proteins according to the invention can be obtained in a reproducible manner and in large amounts. The nucleic acid molecules are integrated into suitable expression vectors, such as exogenous nucleic acid molecules, according to methods familiar to a person skilled in the art, and are introduced into a prokaryotic host cell or a eukaryotic host cell. Such an expression vector preferably contains a regulatable/inducible promoter to which the coding sequence is operably linked. These recombinant vectors are then introduced into suitable host cells such as, e.g., *E. coli* (prokaryote) or *Saccharomyces cerevisiae*, Terato carcinoma cell line PA-1 sc 9117 (Buttner et al., Mol. Cell Biol. 11: 3573–3583 (1991)), insect cells, such as Sf9, and all insect cells transfected with baculovirus vector, and also CHO or COS cells. The transformed or transduced host cells are cultured under conditions which allow for expression of the heterologous or homologous gene. The isolation of the protein can be carried out according to known methods from the host cell or from the culture supernatant of the host cell. Such methods are described for example by Ausubel, et al., Curr. Prof. Mol. Biol. John Wiley & Sons (1992). Also, in vitro reactivation of the protein may be necessary and/or useful using art recognized techniques. Thus, the invention provides methods of producing recombinant PST that can be used, for example, in cell-free synthesis of oligosaccharides, in the study of PST structure and function, and in screening compounds as potential inhibitors of PST enzymatic activity. Soluble PST enzyme is preferred for these uses. For recombinant production of soluble PST, it is preferable to utilize a DNA molecule comprising or consisting of PST coding sequences (i.e., nucleotides 301–1377 in SEQ ID NO: 1 or nucleotides 213–1289 in SEQ ID NO: 7) lacking nucleotides which code for the first 20–30 or more amino acids of the N-terminus. Particularly preferred are DNA molecules comprising nucleotides 330–1289 of SEQ ID NO: 7 and the equivalent section of SEQ ID NO: 1. Expression of recombinant PST may be further enhanced by including in the PST DNA at positions immediately upstream of the first codon and down of the translation termination codon, respectively, 5' and 3' untranslated sequence (e.g., 5' untranslated sequence approximating a consensus sequence [see, e.g., Kozak (1991) J. Biol. Chem. 266: 19867–19870] such as nucleotides 207–212 in SEQ ID NO: 7 and 3' untranslated sequence comprising nucleotides 1293–1304 in SEQ ID NO: 7).

It is further preferred to utilize a host cell that facilitates secretion of the soluble enzyme. For secretion of soluble PST from host cells, the nucleic acid encoding soluble PST is linked, at the 5' end, to nucleic acid encoding a signal peptide capable of directing secretion of proteins in the selected host cell. For example, nucleic acids encoding the protein A signal sequence can be linked to the 5' end of nucleic acid encoding PST for secretion of PST from appropriate host cells, in a manner well known to the skilled artisan.

It is possible to provide a test based upon nucleic acid molecules encoding PST protein, which are then used to detect nucleic acid molecules which code specifically for PST proteins. Such a test can be carried out, e.g., in cells or cell lysates. Such a test can be carried out in accordance with standard nucleic acid diagnostic methods. In such cases, the sample to be examined is brought into contact with a probe which hybridizes with the nucleic acid molecules coding for the PST protein of interest such as nucleotides 301–720 of SEQ ID NO: 1 or sequences specific for 1201 to 1377 of SEQ ID NO: 7. Hybridization between the probe and nucleic acid molecules from the sample indicates the presence of expressed PST proteins. Such methods are known to a person skilled in the art and are for example described in WO 89/06698, EP-A 0 200 362, U.S. Pat. No. 4,915,082, EP-A 0 063 879, EP-A 0 173 251, EP-A 0 128 018. In preferred embodiments of the invention, the nucleic acid molecule of the sample which codes for a PST protein is amplified before testing, e.g. by the well-known PCR technique. A derivatized (labelled) nucleic acid probe is normally used. This probe is brought into contact with a carrier-bound denatured DNA or RNA from the sample and in this process the temperature, ionic strength, pH value and other buffer conditions are selected in such a way that —depending on the length of the nucleic acid molecule sample and the resulting melting temperature of the expected hybrid—the labelled DNA or RNA can bind to homologous DNA or RNA (hybridization, see also J. Mol. Biol. 98: 503 (1975),; Proc. Natl. Acad. Sci. USA 76: (1979). Suitable carriers are membranes or carrier materials based on nitrocellulose reinforced or bound nitrocellulose in a powder form or nylon membranes derivatized with various functional groups (e.g. nitro group).

The hybridized DNA or RNA is then detected by incubating the carrier, after thorough washing and saturation to prevent unspecific binding, with an antibody or antibody fragment. The antibody or antibody fragment is directed towards the substance incorporated into the nucleic acid probe during the derivatization. The antibody is in turn labelled. It is, however, also possible to use a directly labelled DNA. After incubation with the antibodies, it is washed again in order to only detect specifically bound antibody conjugates. The determination is then carried out via the label of the antibody or antibody fragment according to well-known methods.

The detection of the PST expression can be carried out for example as:

in situ hybridization with immobilized whole cells using immobilized tissue smears and isolated metaphase chromosomes, colony hybridization (cells) and plaque hybridization (phages and viruses), Northern hybridization (RNA detection),
serum analysis (e.g. cell type analysis of cells in serum by slot-blot analysis),
after amplification (e.g. PCR technique).

Since PST preferably is regulated on the mRNA level, it is preferred to carry out, for detecting the PST expression, a hybridization with the mRNA of the cell to be examined.

The invention therefore includes a specific method for the detection of nucleic acid molecules which code for a PST protein which is characterized in that the sample to be examined is incubated with a nucleic acid probe which may be selected from the group comprising nucleic acid molecules or specific oligonucleotides which hybridize with the nucleotides 301 to 720 and/or 1201 to 1377 of SEQ ID NO: 1, 633 to 1112 of SEQ ID NO: 7 and their complementary sequences. The nucleic acid probe is incubated with the nucleic acid molecules from the sample and the hybridization of the nucleic acid molecules in the sample and nucleic acid probe is detected, if desired, via a further binding partner.

Thus, PST and its expression is a valuable prognostic marker in tumor diagnostics (metastasis, progress).

Another feature of the invention is oligonucleotide molecules, such as SEQ ID NOS: 3, 4, 5, and 6, as well as (a) nucleotides 237–257, (b) nucleotides 434–451, (c) nucleotides 759–775, and (d) nucleotides 1268–1285 of SEQ ID NO: 7, and their complementary sequences which hybridize to PST coding sequences and may specifically inhibit the expression of PST in mammalian cells. It has been found that when an oligonucleotide molecule reaches a length which is more than about 15 to 17 nucleotides the sequence is unique relative to the entire human genome. Thus, these "$15^+$ meres" are specific to particular regions of the genome. It has been shown that short antisense oligo-nucleotides can be imported into cells and inhibit expression of a gene to which they are targeted (Zamecnik et al., Proc. Natl. Acad. USA 83: 4143 (1986)). In particular, oligonucleotide molecules having 15 to 50, preferably 15 to 25, bases are suitable for use.

Therefore, such oligonucleotide molecules which is complementary to, and designed on the basis of portions of the PST genes described herein are useful for inhibiting the expression of PST.

A further embodiment of the invention is an oligonucleotide molecule which hybridizes in a manner which is specific for nucleic acid molecules of mammalian polysialyl transferase, e.g. with a part or all of SEQ ID NO: 1, or SEQ ID NO: 7.

The term "hybridizes in a manner which is specific for a nucleic acid molecule of mammalian polysialyl transferase" means that such a nucleic acid molecule or oligonucleotide molecule, when transfected into mammalian cells such as human cells, binds to the nucleic acid molecules which code for a polysialyl transferase in said cells. Specific binding occurs if these nucleic acid molecules inhibit the expression of PST in a considerable manner (more than 50%, preferably more than 80%, or more than 90%) and in such fashion that the other metabolism processes of the cell are not impaired.

As is shown by comparing SEQ ID NOS: 2 and 8 and the known sequences of sialyl transferase (Sasaki et al., J. Biol. Chem. 269: 15950–15956 (1994)) and literature cited therein), the region of approx.0 amino acid 141 to approximately amino acid 300 of SEQ ID NOS: 2 and 8 are similar to sialyl motifs of known monosialyl transferases. Accordingly, an oligonucleotide molecule or a nucleic acid molecule which is to hybridize specifically with the PST nucleic acid molecule will at least in its essential part be complementary to sequences in the other regions of SEQ ID NOS: 1, or 7 especially in the coding region of nucleotides 301 to 720 and 1201 to 1377 of SEQ ID NO: 1, 213–632 and 1113–1289 of SEQ ID NO: 7. Especially preferred are oligonucleotides which bind to the PST gene at or in the vicinity of the start codon or the promoter region. Standard hybridization conditions are described in Sambrook et al., supra.

A preferred oligonucleotide molecule interferes in a sequence-specific manner with processes such as the translation of PST mRNA into the protein by binding to PST mRNA. Further oligonucleotide molecules which are suitable for use are oligonucleotide molecules which are complementary to genomic DNA which can interact in forming a triple helical structure (M. Cooney et al., Science 241: 456 (1988) and Duvall-Valentine et al., Proc. Natl. Acad. Sci. USA 89: 504–508 (1992)). Formation of a triple helix prevents expression of the gene normally encoded by the double helix.

Preferred oligonucleotide molecules include oligonucleotide derivatives, such as phosphotriester, methylphosphonates, phosphorothioates or substituted oligonucleotides, such as acridine, interchalating coupled oligonucleotides, or $\alpha$-anomers or $\beta$-anomers (J. J. Toulme and C. Helene, Gene 72: 51–58 (1988)). Phosphorothioates and methylphosphonates are specifically preferred. Such oligo derivatives can be synthesized according to the state of the art, for example by automated technology (S. Beaucage and M. Caruthers, Tetrahedron Lett. 37: 3556 (1981); G. Zon and T. Geiser, Anticanc. Drug Des. 6: 539 (1991); C. A. Stein et al., Pharmacol. Ter. 52: 365 (1991); P. Miller. Biotechnology 9: 358 (1991)). Especially preferred are phosphothioates and methylphosphonates, because they are resistant against serum and intracellular nucleases. Further useful antisense oligonucleotides which are nuclease-resistant are described in P. S. Miller et al., Nucleosides and Nucleotides 6: 769–776 (1985).

It is, in principle, possible to use "naked" antisense oligonucleotide molecules according to the invention, because these oligonucleotides can be taken up by cells non-specifically. However, such oligonucleotides are integrated in the cells at a low efficiency. Therefore, in general, a delivery system for antisense oligos is preferred.

Another aspect of the invention is a soluble complex for targeting an antisense oligonucleotide molecule according to the invention which hybridizes in a manner which is specific for nucleic acid molecules encoding mammalian polysialyl transferase with, e.g., a part or all of SEQ ID NO: 1, or SEQ ID NO: 7 complexed with an oligonucleotide molecule binding agent, which complexes the oligonucleotide molecule under extracellular conditions and releases said oligonucleotide molecule under intracellular conditions as an oligonucleotide molecule specifically bindable to polysialyl transferase encoding nucleic acid molecule.

Such delivery systems are well-known in the state of the art. For example, oligonucleotides are covalently coupled to polycations, such as polylysine (M. Lemaitre et al., Proc. Natl. Acad. Sci. USA 84: 648–652 (1987)). Further delivery systems using polycation conjugates (e.g. transferrin) are described in WO 92/20316, U.S. Pat. No. 5,166,320, WO 92/19281, WO 92/13570, EP-A 0 388 758, WO 93/07283, WO 92/17210, WO 91/17773, WO 93/04701 and transfer peptides as specified in PCT/EP94/01147 are also suitable.

The efficacy of the internalization of the nucleic acid molecules according to the invention in cells can be improved by binding the nucleic acid molecule to amphiphilic molecules, such as polyethylene glycol in a complex. Further preferred are the use of transfection reagents, such as DOTMA (WO 91/06309 and WO 91/17424). Liposomes and dendromers are also useful.

In order to attain cell specificity, the nucleic acid molecules according to the invention can be coupled non-covalently to conjugates from a DNA-binding substance (e.g. polycations) and/or a cell-specific ligand (e.g. protein, preferably PSA specific antibody) (Wu, et al. J. Biol. Chem. 4429–4432 (1987); Wu et al. (1988)). Further, internalization of the nucleic acid molecules in cells is accomplished by means of a soluble DNA carrier system consisting of a chemically synthesized conjugate comprising mannose and lactose as the ligands (P. Midoux et al., Nucl. Acids Res. 21: 871–878 (1993)). EP-A 0 388 758 discloses chemically synthesized transferrin polycation conjugates which form complexes with polyanionic nucleic acid molecules. By means of the binding to the transferrin receptor these complexes can be internalized in the target cells.

It is also known to use conjugates of polylysine and asialoglycoprotein (Wu et al., J. Biol. Chem. 263: 14621–14624 (1988)) or with a galactose ligand (Plank et al., Bioconjugate Chem. 3: 533–539 (1992)) in the complexes. As ligands there were also employed inactivated adenoviruses (Cotten et al., Proc. Natl. Acad. Sci. USA 89: 6094–6098 (1992); Wagner et al., Proc. Natl. Acad. Sci. USA 89: 6099–6103 (1992)) or hemagglutinin infusion peptides (Wagner et al., Proc. Natl. Acad. Sci. USA 89: 7934–7938 (1992)). WO 93/07283 also describes, with regard to non-viral gene transfer, a "2-ligand-system" comprising a DNA-binding (polycationic) portion (substance with affinity towards nucleic acid molecules) and an internalization factor for the take-up of DNA in the cell. To release the complexes from the endosomes into cytoplasm, there may be added to these complexes, as described in WO 93/07283, a socalled endosomolytic agent which corresponds, for example, to a virus or a virus component (e.g. adenovirus or influenza hemagglutinin).

If the carrier for the oligonucleotide molecule is a conjugate from a cell-specific ligand and a DNA binding substance, these substances are preferred to be covalently linked and the linkage typically is a peptide bond. This can be formed, for example, with a water-soluble carbodiimide as described by G. Jung et al., Biochem. Biophys. Res. Comm. 101: 599–606 (1981). An alternative linkage is a disulfide bond.

A cell-specific agent, which can be a natural or synthetic ligand (for example, a protein polypeptide, glycoprotein, etc.) or it can be an antibody or an analogue thereof which specifically binds to a cellular surface structure which then mediates internalization of the bound complex can be, and is preferably used in these systems. Such antibodies are described in Frosch et al., Proc. Natl. Acad. Sci. USA 82: 1194–1198 (1985) and in Molenaar, et al., Canc. Res. 50: 1102–1106 (1990). The antibodies described in Molenaar recognize epitopes on all NCAM isoforms. After binding, these antibodies are internalized.

Typically, the cell-specific binding agent is a ligand which binds to a cell-surface receptor. Preferably receptors are employed which are specific for such tissue cells from which the tumor to be treated originates.

It is specifically preferred to use the antisense oligos for the treatment of tumor diseases involving a high metastasis potential (small cell lung carcinoma, medulloblastoma, Wilms'tumor and lymphoid tumor. See Kern, et al., Leukemia and Lymphoma 12: 1–10 (1993)). Tumor antigens that are suitable for use as surface receptors are, for instance, the tumor antigens.

It is further preferred that the employed cell-specific ligand acts as a substance which facilitates the internalization of the oligonucleotide molecules according to the invention. Such internalization factors are, for example, transferrin or anti-CD4-antibody.

The optimal ratio of the cell-specific binding agent to the oligonucleotide molecule and the oligonucleotide binding agent in the complexes can be determined empirically. When polycations are used, the molar ratio of the components will vary depending on the size of the polycation and the size of the oligonucleotide. To form the complex, the oligonucleotide molecules and carriers are mixed and incubated under conditions conductive to complexation. For example, the oligonucleotide molecule and carrier can be mixed at the appropriate ratio in 2 mol/l NaCl and the solution can be diluted to 0.15 mol/l and filtered to provide an administerable composition.

The oligonucleotide molecules or the molecular complexes of this invention can be administered parenterally. Preferably, it is injected intravenously. The complex is administered in solution in a physiologically acceptable vehicle.

A further object of the invention therefore is the use of a nucleic acid molecule or oligonucleotide molecule or complex according to the invention, for the production of a therapeutic agent for the treatment of tumor therapy, especially for prevention or inhibition of metastasis tumors.

Accordingly, a further aspect of the invention provides methods of retarding or preventing tumor metastasis comprising inhibition of PST activity within the tumor cells. Preferred methods of retarding or preventing tumor metastasis comprise introducing into tumor cells oligonucleotides that specifically bind to all or a portion(s) of nucleic acid encoding proteins having PST activity, most preferably oligonucleotides complementary to all or portions of the sequences set forth in SEQ ID NOS: 1 or 7. Preferably, the tumor chosen is melanoma, small cell lung cancer, or lymphoma. Other tumors which are neuro-ectodermal in nature which express inappropriate levels of PST may also be so treated.

In another aspect, the invention involves methods of modulating cellular interactions and adhesion comprising recombinant expression of exogenous PST in appropriate host cells expressing adhesion proteins, e.g., N-CAM. For this purpose, it is preferably to utilize nucleic acids comprising or consisting of PST coding sequences (i.e., nucleotides 301–1377 in SEQ ID NO: 1 or nucleotides 213–1289 in SEQ ID NO: 7). The PST-encoding nucleic acid can be introduced into the cells through transfection of the cells with PST-encoding DNA or injection of the cells with PST mRNA. In a particular embodiment, such methods include methods of promoting neurite outgrowth on nerve cells and/or substrate cells on which nerve cells are grown. Accordingly, in a further aspect, the invention involves methods of promoting neuroregeneration comprising transplantation of recombinant PST-expressing neuroepithelial cells into tissues exhibiting neurodegeneration.

In accordance with yet another embodiment of the invention, there are provided antibodies generated against the PST proteins disclosed herein. Such antibodies can be employed for studying PST tissue localization, structure of functional domains, purification of PST as well as in diagnostic and therapeutic applications and the like. Preferably, for therapeutic applications, the antibodies employed will be monoclonal antibodies.

The antibodies can be prepared employing standard techniques, as are well known to those of skill in the art, using the invention PST proteins or portions thereof as antigens for antibody production. Both anti-peptide and anti-fusion protein antibodies can be used [see, for example, Current Protocols in Molecular Biology (Ausubel et al. eds.) John Wiley and Sons, N.Y. (1989)]. Factors to consider in selecting portions of the PST protein for use as immunogen (as either a synthetic peptide or a recombinantly produced bacterial fusion protein) include antigenicity, accessibility (i.e., cytoplasmic domains), uniqueness, etc.

The availability of PST-specific antibodies makes possible the application of the technique of immunohistochemistry to monitor the distribution and expression density of the PST protein. In addition PST-specific antibodies can be employed in methods of treating as indicated supra.

Due to the fact that the occurrence of minor errors in the sequencing of DNA sequences cannot be ruled out, it is pointed out that in the event of any discrepancy between the sequence contained in the vector pME7/PST-1 and the sequence stated in SEQ ID NO: 1, the sequence accessible, to the person skilled in the art, from pME7/PST-1 should be resorted to. Other features of the invention will be clear to the skilled artisan and are not presented here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
( A ) LENGTH: 2026 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION:301..1377

( x i ) SEQUENCE DESCRIPTION: SEQ ID NO: 1:

```
GCGACCGCCA CCTCCAATGC ACAAGGTGTC ACATTTGAAA AGAAACCTGA GCCCGGGGGA      60

GAAGGCGCTG AGAGACCCTG GCCTGGCTAG TGCAAACTGC GCGGCAGGGC GCTGGGCAGC     120

CTGGAGAACC CAGAGAGCTC CACCGCAGAC CATCCTAGCG ACCTGATTCT GGGATCTCGG     180

CTCCACGCTC CCTTCGCAAT TTTCAGATTT CTCTCCCTCG ATTATTTCCC CAAAACGGAA     240

CCTTTATACC AAGAGAAGGT GCCGGAGCTG GGGCAACCAG GACTTTCCCG GGCACCCAAG     300

ATG CGC TCC ATT AGA AAA CGG TGG ACC ATC TGC ACT ATA AGT CTA CTT       348
Met Arg Ser Ile Arg Lys Arg Trp Thr Ile Cys Thr Ile Ser Leu Leu
  1               5                  10                  15

CTG ATC TTT TAT AAG ACA AAA GAG ATA GCC AGA ACT GAG GAG CAC CAA       396
Leu Ile Phe Tyr Lys Thr Lys Glu Ile Ala Arg Thr Glu Glu His Gln
             20                  25                  30

GAG ACG CAA CTC ATC GGA GAT GGT GAA TTG TGT TTG AGC AGA TCA CTT       444
Glu Thr Gln Leu Ile Gly Asp Gly Glu Leu Cys Leu Ser Arg Ser Leu
         35                  40                  45

GTC AAC AGC TCT GAT AAA ATC ATT CGG AAG GCT GGC TCA ACC ATC TTC       492
Val Asn Ser Ser Asp Lys Ile Ile Arg Lys Ala Gly Ser Thr Ile Phe
     50                  55                  60

CAA CAT TCT GTA CAA GGC TGG AGA ATC AAT TCT TCT TTA GTC CTG GAG       540
Gln His Ser Val Gln Gly Trp Arg Ile Asn Ser Ser Leu Val Leu Glu
 65                  70                  75                  80

ATA CGG AAG AAC ATT CTC CGT TTC TTA GAT GCT GAA CGT GAT GTC TCT       588
Ile Arg Lys Asn Ile Leu Arg Phe Leu Asp Ala Glu Arg Asp Val Ser
                 85                  90                  95

GTG GTC AAG AGC AGC TTC AAG CCT GGT GAT GTC ATC CAC TAT GTG TTG       636
Val Val Lys Ser Ser Phe Lys Pro Gly Asp Val Ile His Tyr Val Leu
            100                 105                 110
```

```
GAC  AGA  CGC  CGG  ACG  CTA  AAT  ATT  TCC  CAT  GAT  CTG  CAC  AGC  CTC  CTG        684
Asp  Arg  Arg  Arg  Thr  Leu  Asn  Ile  Ser  His  Asp  Leu  His  Ser  Leu  Leu
          115                      120                      125

CCT  GAA  GTT  TCA  CCA  ATG  AAA  AAC  CGC  AGG  TTT  AAG  ACC  TGT  GCT  GTT        732
Pro  Glu  Val  Ser  Pro  Met  Lys  Asn  Arg  Arg  Phe  Lys  Thr  Cys  Ala  Val
     130                      135                      140

GTT  GGA  AAC  TCT  GGC  ATT  CTA  CTA  GAC  AGT  GGA  TGT  GGC  AAG  GAG  ATT        780
Val  Gly  Asn  Ser  Gly  Ile  Leu  Leu  Asp  Ser  Gly  Cys  Gly  Lys  Glu  Ile
145                      150                      155                      160

GAC  AGT  CAC  AAT  TTT  GTA  ATC  AGG  TGC  AAT  CTA  GCT  CCT  GTG  GTG  GAG        828
Asp  Ser  His  Asn  Phe  Val  Ile  Arg  Cys  Asn  Leu  Ala  Pro  Val  Val  Glu
                    165                      170                      175

TTT  GCT  GCG  GAT  GTG  GGG  ACT  AAA  TCA  GAT  TTT  ATT  ACC  ATG  AAC  CCA        876
Phe  Ala  Ala  Asp  Val  Gly  Thr  Lys  Ser  Asp  Phe  Ile  Thr  Met  Asn  Pro
               180                      185                      190

TCA  GTT  GTG  CAG  AGA  GCA  TTT  GGA  GGC  TTT  CGG  AAT  GAG  AGT  GAC  AGA        924
Ser  Val  Val  Gln  Arg  Ala  Phe  Gly  Gly  Phe  Arg  Asn  Glu  Ser  Asp  Arg
               195                      200                      205

GCA  AAA  TTT  GTG  CAT  AGA  CTT  TCC  ATG  CTG  AAT  GAC  AGT  GTC  CTT  TGG        972
Ala  Lys  Phe  Val  His  Arg  Leu  Ser  Met  Leu  Asn  Asp  Ser  Val  Leu  Trp
     210                      215                      220

ATC  CCC  GCT  TTC  ATG  GTC  AAA  GGA  GGA  GAG  AAG  CAC  GTG  GAA  TGG  GTT       1020
Ile  Pro  Ala  Phe  Met  Val  Lys  Gly  Gly  Glu  Lys  His  Val  Glu  Trp  Val
225                      230                      235                      240

AAT  GCA  TTA  ATC  CTT  AAG  AAC  AAG  CTG  AAA  GTG  CGA  ACT  GCC  TAT  CCA       1068
Asn  Ala  Leu  Ile  Leu  Lys  Asn  Lys  Leu  Lys  Val  Arg  Thr  Ala  Tyr  Pro
                    245                      250                      255

TCA  CTG  AGA  CTT  ATT  CAT  GCT  GTC  AGA  GGT  TAC  TGG  CTG  ACC  AAC  AAA       1116
Ser  Leu  Arg  Leu  Ile  His  Ala  Val  Arg  Gly  Tyr  Trp  Leu  Thr  Asn  Lys
               260                      265                      270

GTG  CCC  ATC  AAA  AGA  CCC  AGC  ACA  GGC  CTC  CTC  ATG  TAC  ACA  CTG  GCC       1164
Val  Pro  Ile  Lys  Arg  Pro  Ser  Thr  Gly  Leu  Leu  Met  Tyr  Thr  Leu  Ala
          275                      280                      285

ACC  AGA  TTT  TGT  GAT  GAA  ATT  CAC  CTG  TAT  GGG  TTC  TGG  CCC  TTC  CCT       1212
Thr  Arg  Phe  Cys  Asp  Glu  Ile  His  Leu  Tyr  Gly  Phe  Trp  Pro  Phe  Pro
     290                      295                      300

AAG  GAT  TTG  AAT  GGA  AAA  GCT  GTG  AAA  TAT  CAT  TAC  TAC  GAT  GAC  TTG       1260
Lys  Asp  Leu  Asn  Gly  Lys  Ala  Val  Lys  Tyr  His  Tyr  Tyr  Asp  Asp  Leu
305                      310                      315                      320

AAA  TAT  AGA  TAC  TTT  TCC  AAC  GCA  AGC  CCT  CAC  AGA  ATG  CCA  TTA  GAA       1308
Lys  Tyr  Arg  Tyr  Phe  Ser  Asn  Ala  Ser  Pro  His  Arg  Met  Pro  Leu  Glu
                    325                      330                      335

TTC  AAA  ACC  CTG  AAT  GTG  CTA  CAC  AAC  AGA  GGA  GCA  CTA  AAA  CTG  ACC       1356
Phe  Lys  Thr  Leu  Asn  Val  Leu  His  Asn  Arg  Gly  Ala  Leu  Lys  Leu  Thr
               340                      345                      350

ACA  GGG  AAG  TGC  ATG  AAG  CAA  TAAAGCACAT  ATTGAAGGAT  CAAAACTGGA                 1407
Thr  Gly  Lys  Cys  Met  Lys  Gln
          355

TAGAAACTTT  TTCTAAAGAT  GCTTCTGGAG  ATTTAGAAAC  AGGATCCAAA  ACAAGGCTGG              1467

GGTTCAGCAT  CCACACTGAC  TGAATAGCTG  AAATGGAAGT  CCATGGGAAT  CCACCACCAG              1527

CTGATGAAAT  ACCTGCCAAG  TGCTCTAACT  ATAAATATT   CTGACTTCAA  GGGTCCAGT               1587

AAGTGCCACT  TCCACGAAGA  ATACAGTTTG  AATGTATTAT  CAGTAGTGTT  TACAAGATCC              1647

AACAGTGCAC  TCATCATTAA  TTAGCAAAGC  AAATATGTTC  GTCACTGTGG  GGCAGCCGCT              1707

GTAATGCCAA  GCACACTGGA  AGAGGAACTC  AGGAGCATCA  CGACTCGGAG  CTTGGGAAAT              1767

TAACATCCTT  ATCCGCAGAA  ATGAAGAAGA  AAAAGAATTC  AACAGTGAA   ATCCATGAGA              1827

TGAAGTAACT  TGAAGGAATG  TCTTCAGTCA  GGACACTGAG  AGTGATCATG  TGTGTGTTTT              1887
```

```
GCTTGTGTTT  TTGTTTGTCT  TCTGAAACTT  GTTTTCTTTT  GGGTATGGGG  TGAATAGAAA        1947

TTCATCTGAG  GTACAGAAAT  GGGAAATACA  TGACAGAGAA  AAATAAACAT  CAAACAGTCA        2007

AAAAAAAAAA  AAAAAAAA                                                          2026
```

( 2 ) INFORMATION FOR SEQ ID NO: 2:

( i ) SEQUENCE CHARACTERISTICS:
        ( A ) LENGTH: 359 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Met  Arg  Ser  Ile  Arg  Lys  Arg  Trp  Thr  Ile  Cys  Thr  Ile  Ser  Leu  Leu
 1              5                        10                       15

Leu  Ile  Phe  Tyr  Lys  Thr  Lys  Glu  Ile  Ala  Arg  Thr  Glu  Glu  His  Gln
              20                       25                       30

Glu  Thr  Gln  Leu  Ile  Gly  Asp  Gly  Glu  Leu  Cys  Leu  Ser  Arg  Ser  Leu
                35                       40                       45

Val  Asn  Ser  Ser  Asp  Lys  Ile  Ile  Arg  Lys  Ala  Gly  Ser  Thr  Ile  Phe
     50                       55                       60

Gln  His  Ser  Val  Gln  Gly  Trp  Arg  Ile  Asn  Ser  Ser  Leu  Val  Leu  Glu
65                       70                       75                       80

Ile  Arg  Lys  Asn  Ile  Leu  Arg  Phe  Leu  Asp  Ala  Glu  Arg  Asp  Val  Ser
                85                       90                       95

Val  Val  Lys  Ser  Ser  Phe  Lys  Pro  Gly  Asp  Val  Ile  His  Tyr  Val  Leu
               100                      105                      110

Asp  Arg  Arg  Arg  Thr  Leu  Asn  Ile  Ser  His  Asp  Leu  His  Ser  Leu  Leu
               115                      120                      125

Pro  Glu  Val  Ser  Pro  Met  Lys  Asn  Arg  Arg  Phe  Lys  Thr  Cys  Ala  Val
     130                      135                      140

Val  Gly  Asn  Ser  Gly  Ile  Leu  Leu  Asp  Ser  Gly  Cys  Gly  Lys  Glu  Ile
145                      150                      155                      160

Asp  Ser  His  Asn  Phe  Val  Ile  Arg  Cys  Asn  Leu  Ala  Pro  Val  Val  Glu
               165                      170                      175

Phe  Ala  Ala  Asp  Val  Gly  Thr  Lys  Ser  Asp  Phe  Ile  Thr  Met  Asn  Pro
               180                      185                      190

Ser  Val  Val  Gln  Arg  Ala  Phe  Gly  Gly  Phe  Arg  Asn  Glu  Ser  Asp  Arg
          195                      200                      205

Ala  Lys  Phe  Val  His  Arg  Leu  Ser  Met  Leu  Asn  Asp  Ser  Val  Leu  Trp
     210                      215                      220

Ile  Pro  Ala  Phe  Met  Val  Lys  Gly  Gly  Glu  Lys  His  Val  Glu  Trp  Val
225                      230                      235                      240

Asn  Ala  Leu  Ile  Leu  Lys  Asn  Lys  Leu  Lys  Val  Arg  Thr  Ala  Tyr  Pro
               245                      250                      255

Ser  Leu  Arg  Leu  Ile  His  Ala  Val  Arg  Gly  Tyr  Trp  Leu  Thr  Asn  Lys
               260                      265                      270

Val  Pro  Ile  Lys  Arg  Pro  Ser  Thr  Gly  Leu  Leu  Met  Tyr  Thr  Leu  Ala
               275                      280                      285

Thr  Arg  Phe  Cys  Asp  Glu  Ile  His  Leu  Tyr  Gly  Phe  Trp  Pro  Phe  Pro
     290                      295                      300

Lys  Asp  Leu  Asn  Gly  Lys  Ala  Val  Lys  Tyr  His  Tyr  Tyr  Asp  Asp  Leu
305                      310                      315                      320

Lys  Tyr  Arg  Tyr  Phe  Ser  Asn  Ala  Ser  Pro  His  Arg  Met  Pro  Leu  Glu
               325                      330                      335
```

```
Phe  Lys  Thr  Leu  Asn  Val  Leu  His  Asn  Arg  Gly  Ala  Leu  Lys  Leu  Thr
              340                      345                      350

Thr  Gly  Lys  Cys  Met  Lys  Gln
         355
```

( 2 ) INFORMATION FOR SEQ ID NO: 3:

( i ) SEQUENCE CHARACTERISTICS:
        ( A ) LENGTH: 21 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 3:

ACCATCTGCA CTATAAGTCT A                                         21

( 2 ) INFORMATION FOR SEQ ID NO: 4:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 4:

TTCTTCTTTA GTCCTGGA                                            18

( 2 ) INFORMATION FOR SEQ ID NO: 5:

( i ) SEQUENCE CHARACTERISTICS:
        ( A ) LENGTH: 17 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 5:

GACTAAATCA GATTTTA                                              17

( 2 ) INFORMATION FOR SEQ ID NO: 6:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 6:

CACAGGGAAG TGCATGAA                                           18

( 2 ) INFORMATION FOR SEQ ID NO: 7:

( i ) SEQUENCE CHARACTERISTICS:
        ( A ) LENGTH: 1292 nucleotides
        ( B ) TYPE: nucleic acids
        ( C ) STRANDEDNESS: single
        ( D ) TOPOLOGY: linear ( x i ) SEQUENCE DESCRIPTION: SEQ ID NO: 7:

```
ATG  CGC  TCC  ATT  AGG  AAG  AGG  TGG  ACG  ATC  TGC  ACA  ATA  AGT  CTG  CTC     48
Met  Arg  Ser  Ile  Arg  Lys  Arg  Trp  Thr  Ile  Cys  Thr  Ile  Ser  Leu  Leu
                    5                        10                       15

CTG  ATC  TTT  TAT  AAG  ACA  AAA  GAA  ATA  GCA  AGA  ACT  GAG  GAG  CAC  CAG     96
Leu  Ile  Phe  Tyr  Lys  Thr  Lys  Glu  Ile  Ala  Arg  Thr  Glu  Glu  His  Gln
                    20                       25                       30

GAG  ACG  CAA  CTC  ATC  GGA  GAT  GGT  GAA  TTG  TCT  TTG  AGT  CGG  TCA  CTT    144
Glu  Thr  Gln  Leu  Ile  Gly  Asp  Gly  Glu  Leu  Ser  Leu  Ser  Arg  Ser  Leu
```

|  |  |  |  |  | 35 |  |  |  |  | 40 |  |  |  |  | 45 |  |  |  |
|---|---|---|---|---|---|---|---|---|---|---|---|---|---|---|---|---|---|---|
| GTC | AAT | AGC | TCT | GAT | AAA | ATC | ATT | CGA | AAG | GCT | GGC | TCT | TCA | ATC | TTC | | | 192 |
| Val | Asn 50 | Ser | Ser | Asp | Lys 55 | Ile | Ile | Arg | Lys | Ala 50 | Gly | Ser | Ser | Ile | Phe | | | |

| CAG | CAC | AAT | GTA | GAA | GGT | TGG | AAA | ATC | AAT | TCC | TCT | TTG | GTC | CTA | GAG | 240 |
|---|---|---|---|---|---|---|---|---|---|---|---|---|---|---|---|---|
| Gln 65 | His | Asn | Val | Glu | Gly 70 | Trp | Lys | Ile | Asn | Ser 75 | Ser | Leu | Val | Leu | Glu 80 | |

| ATA | AGG | AAG | AAC | ATA | CTT | CGT | TTC | TTA | GAT | GCA | GAA | CGA | GAT | GTG | TCA | 288 |
|---|---|---|---|---|---|---|---|---|---|---|---|---|---|---|---|---|
| Ile | Arg | Lys | Asn | Ile 85 | Leu | Arg | Phe | Leu | Asp 90 | Ala | Glu | Arg | Asp | Val 95 | Ser | |

| GTG | GTC | AAG | AGC | AGT | TTT | AAG | CCT | GGT | GAT | GTC | ATA | CAC | TAT | GTG | CTT | 336 |
|---|---|---|---|---|---|---|---|---|---|---|---|---|---|---|---|---|
| Val | Val | Lys | Ser 100 | Ser | Phe | Lys | Pro | Gly 105 | Asp | Val | Ile | His | Tyr 110 | Val | Leu | |

| GAC | AGG | CGC | CGG | ACA | CTA | AAC | ATT | TCT | CAT | GAT | CTA | CAT | AGC | CTC | CTA | 384 |
|---|---|---|---|---|---|---|---|---|---|---|---|---|---|---|---|---|
| Asp | Arg | Arg | Arg 115 | Thr | Leu | Asn | Ile | Ser 120 | His | Asp | Leu | His | Ser 125 | Leu | Leu | |

| CCT | GAA | GTT | TCA | CCA | ATG | AAG | AAT | CGC | AGG | TTT | AAG | ACC | TGT | GCA | GTT | 432 |
|---|---|---|---|---|---|---|---|---|---|---|---|---|---|---|---|---|
| Pro | Glu 130 | Val | Ser | Pro | Met 135 | Lys | Asn | Arg | Arg | Phe 140 | Lys | Thr | Cys | Ala | Val | |

| GTT | GGA | AAT | TCT | GGC | ATT | CTG | TTA | GAC | AGT | GAA | TGT | GGA | AAG | GAG | ATT | 480 |
|---|---|---|---|---|---|---|---|---|---|---|---|---|---|---|---|---|
| Val 145 | Gly | Asn | Ser | Gly | Ile 150 | Leu | Leu | Asp | Ser | Glu 155 | Cys | Gly | Lys | Glu | Ile 160 | |

| GAC | AGT | CAC | AAT | TTT | GTA | ATA | AGG | TGT | AAT | CTA | GCT | CCT | GTG | GTG | GAG | 528 |
|---|---|---|---|---|---|---|---|---|---|---|---|---|---|---|---|---|
| Asp | Ser | His | Asn | Phe 165 | Val | Ile | Arg | Cys | Asn 170 | Leu | Ala | Pro | Val | Val 175 | Glu | |

| TTT | GCT | GCA | GAT | GTG | GGA | ACT | AAA | TCA | GAT | TTT | ATT | ACC | ATG | AAT | CCA | 576 |
|---|---|---|---|---|---|---|---|---|---|---|---|---|---|---|---|---|
| Phe | Ala | Ala | Asp 180 | Val | Gly | Thr | Lys | Ser 185 | Asp | Phe | Ile | Thr | Met 190 | Asn | Pro | |

| TCA | GTT | GTA | CAA | AGA | GCA | TTT | GGA | GGC | TTT | CGA | AAT | GAG | AGT | GAC | AGA | 624 |
|---|---|---|---|---|---|---|---|---|---|---|---|---|---|---|---|---|
| Ser | Val | Val 195 | Gln | Arg | Ala | Phe | Gly 200 | Gly | Phe | Arg | Asn | Glu 205 | Ser | Asp | Arg | |

| GAA | AAA | TTT | GTG | CAT | AGA | CTT | TCC | ATG | CTG | AAT | GAC | AGT | GTC | CTT | TGG | 672 |
|---|---|---|---|---|---|---|---|---|---|---|---|---|---|---|---|---|
| Glu | Lys | Phe 210 | Val | His | Arg | Leu | Ser 215 | Met | Let | Asn | Asp | Ser 220 | Val | Leu | Trp | |

| ATT | CCT | GCT | TTC | ATG | GTC | AAA | GGA | GGA | GAG | AAG | CAC | GTG | GAG | TGG | GTT | 720 |
|---|---|---|---|---|---|---|---|---|---|---|---|---|---|---|---|---|
| Ile 225 | Pro | Ala | Phe | Met | Val 230 | Lys | Gly | Gly | Glu | Lys 235 | His | Val | Glu | Trp | Val 240 | |

| AAT | GCA | TTA | ATC | CTT | AAG | AAT | AAA | CTG | AAA | GTG | CGA | ACT | GCC | TAT | CCG | 768 |
|---|---|---|---|---|---|---|---|---|---|---|---|---|---|---|---|---|
| Asn | Ala | Leu | Ile | Leu 245 | Lys | Asn | Lys | Leu | Lys 250 | Val | Arg | Thr | Ala | Tyr 255 | Pro | |

| TCA | TTG | AGA | CTT | ATT | CAT | GCT | GTC | AGA | GGT | TAC | TGG | CTG | ACC | AAC | AAA | 816 |
|---|---|---|---|---|---|---|---|---|---|---|---|---|---|---|---|---|
| Ser | Leu | Arg | Leu 260 | Ile | His | Ala | Val | Arg 265 | Gly | Tyr | Trp | Leu | Thr 270 | Asn | Lys | |

| GTT | CCT | ATC | AAA | AGA | CCC | AGC | ACA | GGT | CTT | CTC | ATG | TAT | ACA | CTT | GCC | 864 |
|---|---|---|---|---|---|---|---|---|---|---|---|---|---|---|---|---|
| Val | Pro | Ile 275 | Lys | Arg | Pro | Ser | Thr 280 | Gly | Leu | Leu | Met | Tyr 285 | Thr | Leu | Ala | |

| ACA | AGA | TTC | TGT | GAT | GAA | ATT | CAC | CTG | TAT | GGA | TTC | TGG | CCC | TTC | CCT | 912 |
|---|---|---|---|---|---|---|---|---|---|---|---|---|---|---|---|---|
| Thr | Arg | Phe 290 | Cys | Asp | Glu | Ile | His 290 | Leu | Tyr | Gly | Phe | Trp 300 | Pro | Phe | Pro | |

| AAG | GAT | TTA | AAT | GGA | AAA | GCG | GTC | AAA | TAT | CAT | TAT | TAT | GAT | GAC | TTA | 960 |
|---|---|---|---|---|---|---|---|---|---|---|---|---|---|---|---|---|
| Lys | Asp 305 | Leu | Asn | Gly | Lys | Ala 310 | Val | Lys | Tyr | His | Tyr 315 | Tyr | Asp | Asp | Leu 320 | |

| AAA | TAT | AGG | TAC | TTT | TCC | AAT | GCA | AGC | CCT | CAC | AGA | ATG | CCA | TTA | GAA | 1008 |
|---|---|---|---|---|---|---|---|---|---|---|---|---|---|---|---|---|
| Lys | Tyr | Arg | Tyr | Phe 325 | Ser | Asn | Ala | Ser | Pro 330 | His | Arg | Met | Pro | Leu 335 | Glu | |

| TTC | AAA | ACA | TTA | AAT | GTG | CTA | CAT | AAT | AGA | GGA | GCT | CTA | AAA | CTG | ACA | 1056 |
|---|---|---|---|---|---|---|---|---|---|---|---|---|---|---|---|---|
| Phe | Lys | Thr | Leu 340 | Asn | Val | Leu | His | Asn 345 | Arg | Gly | Ala | Leu | Lys 350 | Leu | Thr | |

| ACA | GGA | AAG | TGT | GTA | AAG | CAA | TAA | | | | | | | | | 1080 |
|---|---|---|---|---|---|---|---|---|---|---|---|---|---|---|---|---|
| Thr | Gly | Lys | Cys | Val | Lys | Gln | * | | | | | | | | | |

```
                         355                        360
CGCAAACAGG  GCGAGAGGTC  GCTGGGCAGC  GTTCGAGGAC  CAGAGGGAGC  TCGGCCACAG      1140

AAGACCCCAG  TGATCTGATC  CCGGGATCCC  GGCTCCAAGC  TCTCCTCGCA  TTTTACAGAT      1200

TTCACCCCCG  CGACTATCTC  CCCAAAACGG  AGCCTTTATA  TCAAGAGAAG  GTGCGGGAGC      1260

TGGGGCAACC  AGGACTTTCT  CGGGCACCCA  AG                                      1292
```

( 2 ) INFORMATION FOR SEQ ID NO: 8:

( i ) SEQUENCE CHARACTERISTICS:
        ( A ) LENGTH: 1682 nucleotides
        ( B ) TYPE: nucleic acids
        ( C ) STRANDEDNESS: single
        ( D ) TOPOLOGY: linear ( x i ) SEQUENCE DESCRIPTION: SEQ ID NO: 8:

```
ATG  CGC  TCC  ATT  AGG  AAG  AGG  TGG  ACG  ATC  TGC  ACA  ATA  AGT  CTG  CTC      48
Met  Arg  Ser  Ile  Arg  Lys  Arg  Trp  Thr  Ile  Cys  Thr  Ile  Ser  Leu  Leu
                    5                        10                       15

CTG  ATC  TTT  TAT  AAG  ACA  AAA  GAA  ATA  GCA  AGA  ACT  GAG  GAG  CAC  CAG      96
Leu  Ile  Phe  Tyr  Lys  Thr  Lys  Glu  Ile  Ala  Arg  Thr  Glu  Glu  His  Gln
                    20                       25                       30

GAG  ACG  CAA  CTC  ATC  GGA  GAT  GGT  GAA  TTG  TCT  TTG  AGT  CGG  TCA  CTT      144
Glu  Thr  Gln  Leu  Ile  Gly  Asp  Gly  Glu  Leu  Ser  Leu  Ser  Arg  Ser  Leu
          35                       40                       45

GTC  AAT  AGC  TCT  GAT  AAA  ATC  ATT  CGA  AAG  GCT  GGC  TCT  TCA  ATC  TTC      192
Val  Asn  Ser  Ser  Asp  Lys  Ile  Ile  Arg  Lys  Ala  Gly  Ser  Ser  Ile  Phe
          50                       55                       60

CAG  CAC  AAT  GTA  GAA  GGT  TGG  AAA  ATC  AAT  TCC  TCT  TTG  GTC  CTA  GAG      240
Gln  His  Asn  Val  Glu  Gly  Trp  Lys  Ile  Asn  Ser  Ser  Leu  Val  Leu  Glu
65                       70                       75                       80

ATA  AGG  AAG  AAC  ATA  CTT  CGT  TTC  TTA  GAT  GCA  GAA  CGA  GAT  GTG  TCA      288
Ile  Arg  Lys  Asn  Ile  Leu  Arg  Phe  Leu  Asp  Ala  Glu  Arg  Asp  Val  Ser
                    85                       90                       95

GTG  GTC  AAG  AGC  AGT  TTT  AAG  CCT  GGT  GAT  GTC  ATA  CAC  TAT  GTG  CTT      336
Val  Val  Lys  Ser  Ser  Phe  Lys  Pro  Gly  Asp  Val  Ile  His  Tyr  Val  Leu
                    100                      105                      110

GAC  AGG  CGC  CGG  ACA  CTA  AAC  ATT  TCT  CAT  GAT  CTA  CAT  AGC  CTC  CTA      384
Asp  Arg  Arg  Arg  Thr  Leu  Asn  Ile  Ser  His  Asp  Leu  His  Ser  Leu  Leu
          115                      120                      125

CCT  GAA  GTT  TCA  CCA  ATG  AAG  AAT  CGC  AGG  TTT  AAG  ACC  TGT  GCA  GTT      432
Pro  Glu  Val  Ser  Pro  Met  Lys  Asn  Arg  Arg  Phe  Lys  Thr  Cys  Als  Val
130                      135                      140

GTT  GGA  AAT  TCT  GGC  ATT  CTG  TTA  GAC  AGT  GAA  TGT  GGA  AAG  GAG  ATT      480
Val  Gly  Asn  Ser  Gly  Ile  Leu  Leu  Asp  Ser  Glu  Cys  Gly  Lys  Glu  Ile
145                      150                      155                      160

GAC  AGT  CAC  AAT  TTT  GTA  ATA  AGG  TGT  AAT  CTA  GCT  CCT  GTG  GTG  GAG      528
Asp  Ser  His  Asn  Phe  Val  Ile  Arg  Cys  Asn  Leu  Ala  Pro  Val  Val  Glu
                    165                      170                      175

TTT  GCT  GCA  GAT  GTG  GGA  ACT  AAA  TCA  GAT  TTT  ATT  ACC  ATG  AAT  CCA      576
Phe  Ala  Ala  Asp  Val  Gly  Thr  Lys  Ser  Asp  Phe  Ile  Thr  Met  Asn  Pro
                    180                      185                      190

TCA  GTT  GTA  CAA  AGA  GCA  TTT  GGA  GGC  TTT  CGA  AAT  GAG  AGT  GAC  AGA      624
Ser  Val  Val  Gln  Arg  Ala  Phe  Gly  Gly  Phe  Arg  Asn  Glu  Ser  Asp  Arg
                    195                      200                      205

GAA  AAA  TTT  GTG  CAT  AGA  CTT  TCC  ATG  CTG  AAT  GAC  AGT  GTC  CTT  TGG      672
Glu  Lys  Phe  Val  His  Arg  Leu  Ser  Met  Leu  Asn  Asp  Ser  Val  Leu  Trp
          210                      215                      220

ATT  CCT  GCT  TTC  ATG  GTC  AAA  GGA  GGA  GAG  AAG  CAC  GTG  GAG  TGG  GTT      720
Ile  Pro  Ala  Phe  Met  Val  Lys  Gly  Gly  Glu  Lys  His  Val  Glu  Trp  Val
225                      230                      235                      240
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| AAT | GCA | TTA | ATC | CTT | AAG | AAT | AAA | CTG | AAA | GTG | CGA | ACT | GCC | TAT | CCG | 768  |
| Asn | Ala | Leu | Ile | Leu | Lys | Asn | Lys | Leu | Lys | Val | Arg | Thr | Ala | Tyr | Pro |      |
|     |     |     |     | 245 |     |     |     |     | 250 |     |     |     |     | 255 |     |      |
| TCA | TTG | AGA | CTT | ATT | CAT | GCT | GTC | AGA | GGT | TAC | TGG | CTG | ACC | AAC | AAA | 816  |
| Ser | Leu | Arg | Leu | Ile | His | Ala | Val | Arg | Gly | Tyr | Trp | Leu | Thr | Asn | Lys |      |
|     |     |     | 260 |     |     |     |     | 265 |     |     |     |     | 270 |     |     |      |
| GTT | CCT | ATC | AAA | AGA | CCC | AGC | ACA | GGT | CTT | CTC | ATG | TAT | ACA | CTT | GCC | 864  |
| Val | Pro | Ile | Lys | Arg | Pro | Ser | Thr | Gly | Leu | Leu | Met | Tyr | Thr | Ley | Ala |      |
|     |     | 275 |     |     |     |     | 280 |     |     |     |     | 285 |     |     |     |      |
| ACA | AGA | TTC | TGT | GAT | GAA | ATT | CAC | CTG | TAT | GGA | TTC | TGG | CCC | TTC | CCT | 912  |
| Thr | Arg | Phe | Cys | Asp | Glu | Ile | His | Lys | Tyr | Gly | Phe | Trp | Pro | Phe | Pro |      |
|     | 290 |     |     |     |     | 295 |     |     |     |     | 300 |     |     |     |     |      |
| AAG | GAT | TTA | AAT | GGA | AAA | GCG | GTC | AAA | TAT | CAT | TAT | TAT | GAT | GAC | TTA | 960  |
| Lys | Asp | Leu | Asn | Gly | Lys | Arg | Val | Lys | Tyr | His | Tyr | Tyr | Asp | Asp | Leu |      |
| 305 |     |     |     |     | 310 |     |     |     |     | 315 |     |     |     |     | 320 |      |
| AAA | TAT | AGG | TAC | TTT | TCC | AAT | GCA | AGC | CCT | CAC | AGA | ATG | CCA | TTA | GAA | 1008 |
| Lys | Tyr | Arg | Tyr | Phe | Ser | Asn | Ala | Ser | Pro | His | Arg | Met | Pro | Leu | Glu |      |
|     |     |     |     | 325 |     |     |     |     | 330 |     |     |     |     | 335 |     |      |
| TTC | AAA | ACA | TTA | AAT | GTG | CTA | CAT | AAT | AGA | GGA | GCT | CTA | AAA | CTG | ACA | 1056 |
| Phe | Lys | Thr | Leu | Asn | Val | Leu | His | Asn | Arg | Gly | Ala | Leu | Lys | Leu | Thr |      |
|     |     |     | 340 |     |     |     |     | 345 |     |     |     |     | 350 |     |     |      |
| ACA | GGA | AAG | TGT | GTA | AAG | CAA | TAA |     |     |     |     |     |     |     |     | 1080 |
| Thr | Gly | Lys | Cys | Val | Lys | Gln | *   |     |     |     |     |     |     |     |     |      |
|     |     | 355 |     |     |     |     | 360 |     |     |     |     |     |     |     |     |      |

| | | | | |
|---|---|---|---|---|
| AGCACATTTT | GAAACAAACA | ATATGCACTT | CTTTTCTGAG | ATGCTTCCGA | AGATTTGAAA | 1140 |
| ATAGGATCCA | AAACACGGCT | GGGTTTCAGC | ATCCACCAAT | GAACTGAAAG | GTGAATAAAG | 1200 |
| GACGTTCATG | AGAAATCGAC | TACCAGCTGA | TGAAATACCT | GCAAAGTGCT | CTAAAAATTA | 1260 |
| AATATTTTGA | CTTTAAGGGT | CCTAGTAAGT | GCCACTTCCA | CTAAGAATAC | AGTTTGAATG | 1320 |
| TATAATCAGT | AGTGTTTACA | AGATCCAACA | GTGCACTCAT | CATTAGTTAA | CAAAGCAAAT | 1380 |
| ATGTTCATCA | CTGTCAGGCT | GCCCACAGCA | ACACCAAGCA | TATTAGAAGA | GGAACCCCAG | 1440 |
| GAACGCAACT | CAGACCTTGG | GAAATTAAAC | CATCCTTGTC | AGCAGAAGCC | AAGATGGAAG | 1500 |
| CAGTTTGAGC | AATGAAATCC | GTAAGATTAA | ACAACTCAAG | TAAATGCTTC | AGTCAGGACT | 1560 |
| CTGAGTCTGA | TCATGAATTT | TATGTTTTAA | TTTATGTTTT | TTTTTTGTC  | TTCTGGAATC | 1620 |
| TCTTTTGGTT | TGGATATTGG | GATGCTTAGA | AATCCTTTCT | GAGATGCATA | TGAGTGAGGA | 1680 |
| AA | | | | | | 1682 |

We claim:

1. An isolated nucleic acid molecule consisting of from about 10 nucleotides to about 50 nucleotides wherein said isolated nucleic acid molecule hybridizes to a nucleic acid molecule which encodes a polysialyl trasferase, and has a nucleotide sequence selected from the group consisting of; the nucleotide sequence of SEQ ID NO: 1, the nucleotide sequence of SEQ ID NO: 7, and the nucleotide sequence of SEQ ID NO: 8.

2. The isolated nucleic acid molecule of claim 1, which hybridizes to SEQ ID NO: 1.

3. The isolated nucleic acid molecule of claim 1, which hybridizes to SEQ ID NO: 7.

4. The isolated nucleic acid molecule of claim 1, which hybridizes to SEQ ID NO: 8.

5. The isolated nucleic acid molecule of claim 1, consisting of from about 16 to about 40 nucleotides.

6. The isolated nucleic acid molecule of claim 1, consisting of from about 25 to about 30 nucleotides.

7. The isolated nucleic acid molecule of claim 1 selected from the group consisting of: SEQ ID NO: 3, SEQ ID NO: 4, SEQ ID NO: 5 and SEQ ID NO: 6, or the complement thereof.

8. The isolated nucleic acid molecule of claim 1, consisting of nucleotides 237–257 of SEQ ID NO: 7, nucleotides 434–451 of SEQ ID NO: 7, nucleotides 759–775 of SEQ ID NO: 7, or nucleotides 1268–1285 of SEQ ID NO: 7, or the complement thereto.

* * * * *

UNITED STATES PATENT AND TRADEMARK OFFICE
CERTIFICATE OF CORRECTION

PATENT NO. : 5,849,904
DATED : December 15, 1998
INVENTOR(S) : Gerardy-Schahn et al.

It is certified that error appears in the above-identified patent and that said Letters Patent is hereby corrected as shown below:

On the cover, in the section titled Other Publications, column 2, line 7, before "Microbiol." add --Mol.--.

On the cover, in the section titled Other Publications, column 2, line 10, change "Bio." to ---Biol.--.

On the cover, in the section titled Other Publications, column 2, line 24, change "-60" to the Greek letter --α--.

On the cover, in the section titled Other Publications, column 2, line 36, change "endoneuramindase" to --endoneuraminidase--.

On the cover, in the section titled Other Publications, column 2, line 39, chnage "Synthease" to --Synthase--.

In column 3, line 26, change "a-2,3-" to -- α-2,3- --.

UNITED STATES PATENT AND TRADEMARK OFFICE
CERTIFICATE OF CORRECTION

PATENT NO. : 5,849,904
DATED : December 15, 1998
INVENTOR(S) : Gerardy-Schahn et al.

It is certified that error appears in the above-identified patent and that said Letters Patent is hereby corrected as shown below:

In column 8, line 51, before "24 mol)" add -- ( --.

In column 8, line 52, after "(0.186 ml" delete -- ) --.

In column 9, line 15, change "oligo-deoxynucleotides" to --oligodeoxynucleotides--.

In column 9, line 22, change "pmol" to --µmol--.

In column 11, line 64, change "tricyc lo" to --tricyclo--.

In column 12, line 32, change "2.4-$10^7$" to --2.4x$10^7$--.

In column 12, line 46, change "pHS" to pHβ--.

In column 13, line 7, change "2-$10^6$" to --2x$10^6$--.

In column 20, line 21, change "in" to --In--.

UNITED STATES PATENT AND TRADEMARK OFFICE
CERTIFICATE OF CORRECTION

PATENT NO. : 5,849,904

DATED : December 15, 1998

INVENTOR(S) : Gerardy-Schahn et al.

It is certified that error appears in the above-identified patent and that said Letters Patent is hereby corrected as shown below:

In column 21, line 8, change "Encodina" to --Encoding--.

In column 23, line 2, change "a" to the Greek letter --α--.

In column 25, line 38, change "beings" to --being--.

In column 25, line 40, change "Hötke" to --Höltke--.

In column 25, line 42, change "t issue" to --tissue--.

In column 25, line 65, change "calorimetric" to --colorimetric--.

In column 32, line 13, change "conductive" to --conducive--.

UNITED STATES PATENT AND TRADEMARK OFFICE
CERTIFICATE OF CORRECTION

PATENT NO.   : 5,849,904
DATED        : December 15, 1998
INVENTOR(S)  : Gerardy-Schahn  et al.

It is certified that error appears in the above-identified patent and that said Letters Patent is hereby corrected as shown below:

In column 32, line 45, change "preferably" to --preferable--.

Signed and Sealed this

Tenth Day of August, 1999

Q. TODD DICKINSON

*Attest:*

*Attesting Officer*    Acting Commissioner of Patents and Trademarks